(12) United States Patent
Menon et al.

(10) Patent No.: US 12,364,582 B2
(45) Date of Patent: Jul. 22, 2025

(54) GENERATING A 3D-PRINTED MEDICAL APPLIANCE TREATMENT PLAN AND PROVIDING 3D-PRINTED MEDICAL APPLIANCES IN ACCORDANCE THEREWITH

(71) Applicant: Smylio Inc., Fremont, CA (US)

(72) Inventors: Renjith Menon, Campbell, CA (US); Nichole Garcia, Laguna Beach, CA (US); Henry Chan, San Jose, CA (US)

(73) Assignee: Smylio Inc., Fremont, CA (US)

( * ) Notice: Subject to any disclaimer, the term of this patent is extended or adjusted under 35 U.S.C. 154(b) by 874 days.

(21) Appl. No.: 17/053,975

(22) PCT Filed: May 9, 2019

(86) PCT No.: PCT/US2019/031635
§ 371 (c)(1),
(2) Date: Nov. 9, 2020

(87) PCT Pub. No.: WO2019/217764
PCT Pub. Date: Nov. 14, 2019

(65) Prior Publication Data
US 2021/0236251 A1 Aug. 5, 2021

Related U.S. Application Data

(60) Provisional application No. 62/669,312, filed on May 9, 2018.

(51) Int. Cl.
*A61C 13/00* (2006.01)
*A61C 7/00* (2006.01)
(Continued)

(52) U.S. Cl.
CPC .......... *A61C 13/0019* (2013.01); *A61C 7/002* (2013.01); *A61C 7/08* (2013.01);
(Continued)

(58) Field of Classification Search
USPC .......................................... 705/2–3
See application file for complete search history.

(56) References Cited

U.S. PATENT DOCUMENTS 11,000,334 B1 * 5/2021 Young .................... G06T 7/251
2017/0340414 A1 * 11/2017 Janzadeh ................ A61C 7/08
(Continued)

OTHER PUBLICATIONS

Shuai, L., Kiaran, M., Morris, J., Alexander, A., Kuhlmann, J., Vrieze, T., . . . Matsumoto, J. (2017). Anatomic modeling using 3D printing: Quality assurance and optimization. 3D Printing in Medicine, 3(1) doi:http://dx.doi.org/10.1186/s41205-017-0014-3 (Year: 2017).*

(Continued)

*Primary Examiner* — Bennett Stephen Erickson
(74) *Attorney, Agent, or Firm* — Ahmann Kloke LLP

(57) ABSTRACT

A system and method for generating a 3D-printed medical appliance treatment plan and providing a set of 3D-printed medical appliances in accordance therewith, the method comprising: generating a dynamic 3D-printed medical appliance treatment plan generation model; obtaining a patient record; receiving 3D scanning data of the patient; generating a 3D-printed medical appliance treatment plan by applying the patient record and the 3D scanning data to the dynamic 3D-printed medical appliance treatment plan generation model; providing the 3D-printed medical appliance treatment plan to a medical practitioner; providing a manufacturing request to a manufacturer system for manufacturing a set of 3D-printed medical appliances; providing the set of 3D-printed medical appliances to the patient; receiving feedback from the medical practitioner regarding the 3D-printed medical appliance treatment plan; modifying the dynamic 3D-printed medical appliance treatment plan generation model based on the feedback.

19 Claims, 21 Drawing Sheets

(51) Int. Cl.
  *A61C 7/08*    (2006.01)
  *B33Y 50/00*   (2015.01)
  *B33Y 80/00*   (2015.01)
  *G06N 20/00*   (2019.01)
  *G16H 10/60*   (2018.01)

(52) U.S. Cl.
  CPC ............... *B33Y 50/00* (2014.12); *B33Y 80/00* (2014.12); *G06N 20/00* (2019.01); *G16H 10/60* (2018.01)

(56) References Cited

U.S. PATENT DOCUMENTS

| | | |
|---|---|---|
| 2017/0360578 A1 | 12/2017 | Shin |
| 2018/0042705 A1 | 2/2018 | Howe |
| 2019/0175303 A1* | 6/2019 | Akopov ............... A61C 9/0053 |
| 2021/0346091 A1* | 11/2021 | Haslam .................. G16H 30/40 |
| 2022/0183991 A1* | 6/2022 | Daya ......................... A61J 3/06 |

OTHER PUBLICATIONS

International Application No. PCT/US2019/031635, International Search Report and Written Opinion dated Jul. 25, 2019.

* cited by examiner

GENERATING A 3D-PRINTED MEDICAL APPLIANCE TREATMENT PLAN AND PROVIDING 3D-PRINTED MEDICAL APPLIANCES IN ACCORDANCE THEREWITH

CROSS-REFERENCE TO RELATED APPLICATIONS

This application is a national phase application pursuant to 35 U.S.C. § 371 of International Application No. PCT/US2019/031635 filed May 9, 2019, which claims priority to U.S. Provisional Patent Application Ser. No. 62/669,312 filed May 9, 2018, the disclosures of which are incorporated by reference herein.

DETAILED DESCRIPTION

Figure 1:
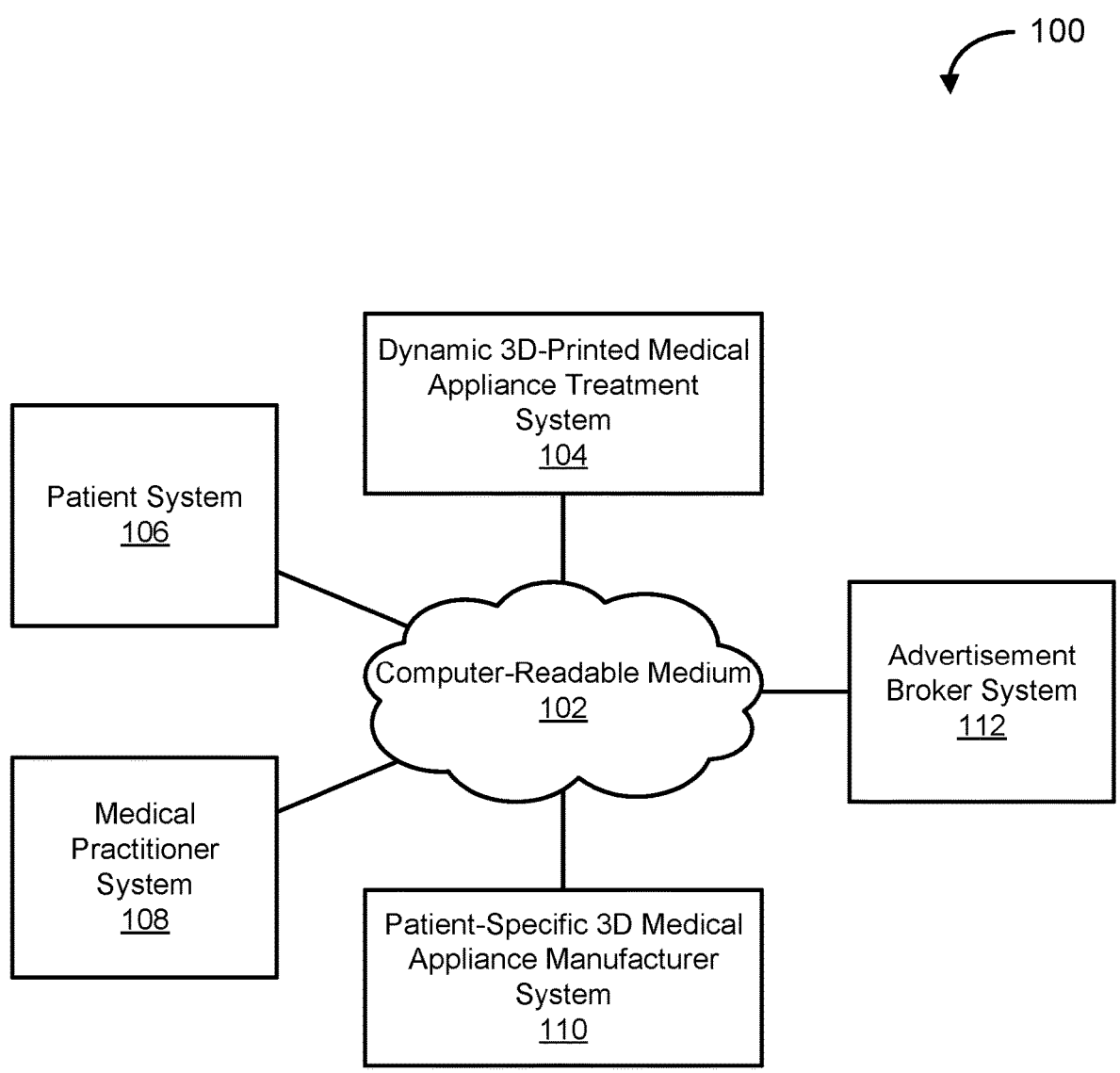
FIG. 1 is a block diagram of an example of a system for providing medical treatment that includes a 3D-printed medical appliance.

FIG. 1 is a block diagram 100 of an example of a system for providing medical treatment that includes a 3D-printed medical appliance. As used in this paper, 3D-printed is intended to include larger dimensions, such as 4D, but to exclude smaller dimensions, such as 2D. For example, aligners can be used to aid in the process of building teeth from a patient's own stem cells. The aligners would aid in the process by holding the structures together and enabling the delivery of enzymes, proteins, biochemicals that can aid in the successful growth of the tooth or teeth. Such aligners are referred to as "4D." This concept is illustrated in FIGS. 17-21. The system of the example of FIG. 1 includes a computer-readable medium 102, a dynamic 3D-printed medical appliance treatment system 104 coupled to the computer-readable medium 102, a patient system 106 coupled to the computer-readable medium 102, a medical practitioner system 108 coupled to the computer-readable medium 102, a patient-specific 3D medical appliance manufacturer system 110 coupled to the computer-readable medium 102, and an advertisement broker system 112 coupled to the computer-readable medium 102.

The computer-readable medium 102 is intended to represent a variety of potentially applicable technologies. For example, the computer-readable medium 102 can be used to form a network or part of a network. Where two components are co-located on a device, the computer-readable medium 102 can include a bus or other data conduit or plane. Where a first component is co-located on one device and a second component is located on a different device, the computer-readable medium 102 can include a wireless or wired back-end network or LAN. The computer-readable medium 102 can also encompass a relevant portion of a WAN or other network, if applicable.

As used in this paper, a "computer-readable medium" is intended to include all mediums that are statutory (e.g., in the United States, under 35 U.S.C. 101), and to specifically exclude all mediums that are non-statutory in nature to the extent that the exclusion is necessary for a claim that includes the computer-readable medium to be valid. Known statutory computer-readable mediums include hardware (e.g., registers, random access memory (RAM), non-volatile (NV) storage, to name a few), but may or may not be limited to hardware.

Applicable systems or devices described in this paper can be implemented as a computer system, a plurality of computer systems, or parts of a computer system or a plurality of computer systems. In general, a computer system will include a processor, memory, non-volatile storage, and an interface and the examples described in this paper assume a stored program architecture, though that is not an explicit requirement of the machine. A typical computer system will usually include at least a processor, memory, and a device (e.g., a bus) coupling the memory to the processor. The processor can be, for example, a general-purpose central processing unit (CPU), such as a microprocessor, or a special-purpose processor, such as a microcontroller. A typical CPU includes a control unit, arithmetic logic unit (ALU), and memory (generally including a special group of memory cells called registers).

The memory can include, by way of example but not limitation, random access memory (RAM), such as dynamic RAM (DRAM) and static RAM (SRAM). The memory can be local, remote, or distributed. The bus can also couple the processor to non-volatile storage. The non-volatile storage is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software on the computer system. The non-volatile storage can be local, remote, or distributed. The non-volatile storage is optional because systems can be created with all applicable data available in memory.

In stored program architectures, software is typically stored in the non-volatile storage. Indeed, for large programs, it may not even be possible to store the entire program in the memory. Nevertheless, it should be understood that for software to run, if necessary, it is moved to a computer-readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at an applicable known or convenient location (from non-volatile storage to hardware registers) when the software program is referred to as "implemented in a computer-readable storage medium." A processor is considered to be "configured to execute a program" when at least one value associated with the program is stored in a register readable by the processor.

In one example of operation, a computer system can be controlled by operating system software, which is a software program that includes a file management system, such as a disk operating system. One example of operating system software with associated file management system software is the family of operating systems known as Windows® from Microsoft Corporation of Redmond, Washington, and their associated file management systems. Another example of operating system software with its associated file management system software is the Linux operating system and its associated file management system. The file management system is typically stored in the non-volatile storage and causes the processor to execute the various acts required by the operating system to input and output data and to store data in the memory, including storing files on the non-volatile storage.

The bus can also couple the processor to the interface. The interface can include one or more input and/or output (I/O) devices. The I/O devices can include, by way of example but not limitation, a keyboard, a mouse or other pointing device, disk drives, printers, a scanner, and other I/O devices, including a display device. The display device can include, by way of example but not limitation, a cathode ray tube (CRT), liquid crystal display (LCD), or some other applicable known or convenient display device. The interface can include one or more modem or network interface. It will be appreciated that a modem or network interface can be considered to be part of the computer system. The interface can include an analog modem, ISDN modem, cable modem, token ring interface, satellite transmission interface (e.g. "direct PC"), or other interfaces for coupling a computer system to other computer systems. Interfaces enable computer systems and other devices to be coupled together in a network.

The computer systems can be compatible with or implemented as part of or through a cloud-based computing system. As used in this paper, a cloud-based computing system is a system that provides virtualized computing resources, software and/or information to client devices. The computing resources, software and/or information can be virtualized by maintaining centralized services and resources that the edge devices can access over a communication interface, such as a network. "Cloud" may be a marketing term and for the purposes of this paper can include any of the networks described herein. The cloud-based computing system can involve a subscription for services or use a utility pricing model. Users can access the protocols of the cloud-based computing system through a web browser or other container application located on their client device.

A computer system can be implemented as an engine, as part of an engine, or through multiple engines. As used in this paper, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors, or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the FIGS. in this paper.

The engines described in this paper, or the engines through which the systems and devices described in this paper can be implemented, can be cloud-based engines. As used in this paper, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used in this paper, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a general- or specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described in this paper.

Datastores can include data structures. As used in this paper, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described in this paper, can be cloud-based datastores. A cloud-based datastore is a datastore that is compatible with cloud-based computing systems and engines.

The dynamic 3D-printed medical appliance treatment system 104 is intended to represent hardware configured to provide treatment to patients using at least one 3D-printed medical appliance. In a specific implementation, the dynamic 3D-printed medical appliance treatment system 104 includes applicable computing devices to be operated by a service provider. Depending upon context, a multi-device treatment is appropriate, the 3D-printed medical appliance treatment includes medical treatment using a series of patient-specific 3D-printed medical appliances, such as aligners (and retainers) for orthodontic treatment, helmets for plagiocephaly (flat head syndrome) treatment, devices suitable for aesthetic treatments such as belts or other accessories that grow smaller in accordance with a weight loss regimen, and so on. Depending upon context, dynamic 3D-printed appliances may be employed outside of medical/dental fields, including beauty, gaming, toys, aerospace, automobiles, energy, etc. Depending upon context, a single-device treatment of a condition, amelioration of an issue, or improvement of aesthetics, is appropriate, such as an on-demand optical frame and lenses customized for a face or head shape and prescription, on-demand ear plugs, ear buds, or hearing aids customized for ear shape, grips for an automobile steering wheel, bicycle handlebars, or the like that are customized for a hand shape, custom-shaped printed clothing or accessories, or the like. In a specific implementation, the 3D-printed medical appliance treatment service includes selection of a medical practitioner suitable for a specific patient, determination of a treatment plan suitable for a specific patient and/or practitioner, selection of a 3D-printed medical appliance manufacturer and suitable for a specific patient and/or practitioner.

In a specific implementation, in performing selection of a medical practitioner, the dynamic 3D-printed medical appliance treatment system 104 is configured to generate a dynamic medical practitioner matching recommendation model. In a specific implementation, the dynamic medical practitioner matching recommendation model is used to match a patient record and preferences to one or more potential practitioner candidates. In a specific implementation, a patient record includes attribute information (e.g., age, gender, race, residence, etc.) of a patient and information on a pre-treatment state (e.g., pre-treatment tooth arrangement) of a patient, which may be obtained, for example, from a picture taken by the patient. In a specific implementation, patient preferences may include a geographical location, a budget range, pain levels throughout the treatment, a treatment duration, pre- and post-treatment state (e.g., aesthetic appearance), automatic or manual, virtual reality (VR)/augmented reality (AR), etc. In a specific implementation, in performing selection of a medical practitioner, the dynamic 3D-printed medical appliance treatment system 104 applies a patient record and patient preferences to the dynamic medical practitioner matching recommendation model to perform matching of medical practitioners.

In a specific implementation, in performing selection of a medical practitioner, the dynamic 3D-printed medical appliance treatment system 104 is configured to organize a practitioner referral auction. In a specific implementation, in organizing a practitioner referral auction, the dynamic 3D-printed medical appliance treatment system 104 selects a plurality of medical practitioners that generally match a patient record and patient preferences, and sends invitation to the practitioner referral auction to the selected medical practitioners. Depending upon implementation-specific or other considerations, the dynamic 3D-printed medical appliance treatment system 104 may employ the dynamic medical practitioner matching recommendation model for selection of the medical practitioners for auction. In a specific implementation, participants can join an auction real-time or asynchronously based on pre-sets.

In a specific implementation, in performing determination of a treatment plan, the dynamic 3D-printed medical appliance treatment system 104 is configured to generate a dynamic 3D medical appliance treatment plan generation model. In a specific implementation, the dynamic 3D medical appliance treatment plan generation model is a data structure based on a patient record and treatment conditions. In a specific implementation, a treatment plan may include an expected post-treatment state of the patient's body part (e.g., final position data), transitioning states of the patient's body part, a treatment term (e.g., length of time and phases), expected pain levels, an estimated price, types and designs of 3D-printed medical appliances to be used for each of different phases of the treatment, and manner and duration of attaching 3D-printed medical appliances, and so on. For example, a 3D (or 4D or greater dimensional) animation to show transition from a pre-treatment state to a post-treatment state may be generated for display on screen and/or in AR/VR. In a specific implementation, treatment conditions include the same information as patient preferences, a budget range, a duration of medical treatment, a post-treatment state (e.g., post-treatment tooth arrangement), an acceptable pain level, and so on. In a specific implementation, in performing determination of a treatment plan, the dynamic 3D-printed medical appliance treatment system 104 applies a patient record and treatment conditions to the dynamic 3D medical appliance treatment plan generation model to perform determination of a treatment plan.

In a specific implementation, in performing selection of a 3D-printed medical appliance manufacturer, the dynamic 3D-printed medical appliance treatment system 104 is configured to generate a dynamic manufacturer selection model. In a specific implementation, the dynamic manufacturer selection model matches a treatment plan with manufacturer records to determine one or more potential manufacturer candidates. In a specific implementation, a manufacturer record includes manufacturer information such as a geographical location, expected delivery time, manufactured appliance type and design, price range, on-time delivery rating, practitioner rating, and patient rating. In a specific implementation, in selecting a 3D-printed medical appliance manufacturer, the dynamic 3D-printed medical appliance treatment system 104 applies a patient record and a treatment plan to the dynamic manufacturer selection model to match 3D-printed medical appliance manufacturers.

Depending upon implementation-specific or other considerations, one or more functionalities of the dynamic 3D-printed medical appliance treatment system 104 may be distributed locally on applicable systems such as the medical practitioner system 108 and the patient-specific 3D medical appliance manufacturer system 110. For example, the medical practitioner system 108 and/or the patient-specific 3D medical appliance manufacturer system 110 may locally install an application including the dynamic 3D medical appliance treatment plan generation model for generation of a treatment plan. In another example, the medical practitioner system 108 may locally install an application including the dynamic manufacturer selection model for selection of 3D-printed medical appliance manufacturer.

The patient system 106 is intended to represent various applicable computing device(s) to be operated by a patient, such as a smartphone, tablet, laptop, desktop computer, smart TV, smart watch, smart speaker, IoT devices, or the like. In a specific implementation, the patient system 106 is configured to receive patient attribute information, which is used to generate a patient record. In a specific implementation, the patient system 106 is configured to capture a patient's body part image (e.g., tooth arrangement picture) to be used for the dynamic 3D-printed medical appliance treatment system 104 to determine a patient's pre-treatment state, and send the captured patient's body part image. In a specific implementation, the patient system 106 is configured to receive information on matched medical practitioners, such that a patient can select a medical practitioner. In a specific implementation, the patient system 106 is configured to receive information on a treatment plan, such that a patient consents to the treatment plan. In a specific implementation, the patient system 106 is configured to receive information on selected manufacturers, such that a patient selects a manufacturer by which a 3D-printed medical appliance is to be manufactured.

The medical practitioner system 108 is intended to represent applicable computing device(s) to be operated by a medical practitioner, such as a smartphone, tablet, laptop, desktop computer, smart TV, smart watch, smart speaker, IoT devices, or the like. In a specific implementation, the medical practitioner system 108, at least one components of the medical practitioner system 108 and/or devices coupled to the medical practitioner system 108 may be provided at a facility of a medical provider (practitioner). In a specific implementation, the medical practitioner system 108 is configured to receive user inputs regarding practitioner attribute information and sends the user inputs for generating a medical practitioner record. In a specific implementation, the medical practitioner system 108 is configured to capture a patient's body part 3D image (e.g., tooth arrangement 3D scanning image) to be used for the dynamic 3D-printed medical appliance treatment system 104 to generate a treatment plan, and send the captured patient's body part 3D image. In a specific implementation, the medical practitioner system 108 is configured to receive information on a patient record, a patient's preference, and/or treatment conditions, for review by a medical practitioner. In a specific implementation, the medical practitioner system 108 is configured to receive information on a treatment plan, for review by a medical practitioner. In a specific implementation, the medical practitioner system 108 is configured to receive information on selected manufacturers, such that a medical practitioner selects a manufacturer by which a 3D-printed medical appliance is to be manufactured.

In a specific implementation, the medical practitioner system 108 is configured to manufacture a trial 3D-printed medical appliance, such that a patient visiting a medical practitioner can try out a 3D-printed medical appliance before starting a 3D-printed medical appliance treatment. For example, the trial 3D-printed medical appliance can have a patient-specific shape formed to fit the patient's body part, in particular a current state of the patient's body part. In a specific implementation, a trial aligner could be referred to as a no-movement tray or a zero-stage tray. Trial aligners are a subset of trial medical devices, which can also be referred to as no-movement medical devices and zero-stage medical devices. In another specific implementation, a trial aligner could be referred to as an initial-movement tray that is designed to cause initial movement of the patient's body part. In both contexts, the aligner may be referred to as a starter aligner.

In a specific implementation, the medical practitioner system 108 is configured to manufacture a starter 3D-printed medical appliance, such that a patient visiting a medical practitioner can start with a 3D-printed medical appliance as a first of a set of 3D-printed medical appliance treatment. For example, the starter 3D-printed medical appliance can have a shape formed to move the patient's body part to a first stage toward a final position. The starter 3D-printed medical appliance can be printed from current records with some computation, but the computational requirements are not expected to be prohibitive; a patient will still be able to get starter 3D-printed medical appliances at the end of an appointment of industry-expected length, and potentially an entire set if 3D-printing is sufficiently fast. A starter aligner could be referred to as a pre-programmed movement tray or a stage one tray. A starter aligner can also be a trial aligner, in which case it could be referred to as a no-movement tray or a zero-stage tray. Starter aligners are a subset of starter medical devices, which can also be referred to as no-movement medical devices and zero-stage medical devices or pre-programmed movement medical devices and stage one medical devices.

In a specific implementation, the medical practitioner system 108 is configured to manufacture a reboot 3D-printed medical appliance, such that a patient visiting a medical practitioner can reboot with a 3D-printed medical appliance after one of a set of 3D-printed medical appliances is lost or broken. For example, the reboot 3D-printed medical appliance can have a shape formed to move the patient's body part from a current stage toward a final position, replacing as-of-yet unused medical appliances in favor of a new set. Advantageously, reboot aligners can start a little further along than the lost or broken aligner (assuming it was worn before it was lost), and reboot aligners can incorporate corrections to address dental relapse. The reboot 3D-printed medical appliance can be printed from current records with some computation, but the computational requirements are not expected to be prohibitive; a patient will still be able to get reboot 3D-printed medical appliances at the end of an appointment of industry-expected length, and potentially an entire set if 3D-printing is sufficiently fast. A reboot aligner could be referred to as a pre-programmed movement tray or a stage one reset tray. Reboot aligners are a subset of reboot medical devices, which can also be referred to as pre-programmed movement medical devices and stage one reset medical devices. Boot medical devices are superset of trial medical devices, starter medical devices, and reboot medical devices, and are intended to represent first medical devices from a boot date (e.g., a first appointment or a later appointment).

The patient-specific 3D medical appliance manufacturer system 110 is intended to represent various applicable computing device(s) to be operated by a 3D-printed medical appliance manufacturer, such as a smartphone, tablet, laptop, desktop computer, smart TV, smart watch, smart speaker, IoT devices, or the like. In a specific implementation, the patient-specific 3D medical appliance manufacturer system 110, at least one components of the medical practitioner system 108, and/or devices coupled to the medical practitioner system 108 may be provided at a facility of a 3D-printed medical appliance manufacturer. In a specific implementation, the patient-specific 3D medical appliance manufacturer system 110 is configured to receive specifications for 3D medical appliances for use in a treatment plan. The patient-specific 3D medical appliance manufacturer system 110 may or may not also receive 3D print specifications, for setting of 3D printing. In a specific implementation, the medical practitioner system 108 is configured to manufacture patient-specific 3D medical appliances based on the treatment, such that the manufactured appliances are delivered to a patient directly or through a medical practitioner.

The advertisement broker system 112 is intended to represent hardware configured to provide advertisement service for 3D medical treatment related business. In a specific implementation, 3D medical treatment related business may include medical providers including medical practitioners and a 3D-printed medical appliance manufacturers. In a specific implementation, advertisement provided through the advertisement service may include images of patient's body part before and after a 3D-printed medical appliance treatment. In a specific implementation, in performing selection of advertisement (e.g., advertisement images), the advertisement broker system 112 is configured to generate a dynamic advertisement selection model. In a specific implementation, the dynamic advertisement selection model is a computer algorithm configured to determine one or more advertisement images that are considered to match attributes (e.g., age, gender, race, income level, etc.) of target advertisement receivers. Further, in a specific implementation, in performing selection of advertisement, the advertisement broker system 112 sends information on the advertisement to a patient system 106 and/or a medical practitioner system 108 for obtaining consent of a patient and/or a medical practitioner. A go-to-market solution is described later with reference to FIG. 16.

In an example of operation of the system shown by way of example in FIG. 1, the patient system 106 provides patient body part images to the dynamic 3D-printed medical appliance treatment system 104. The dynamic 3D-printed medical appliance treatment system 104 generates a dynamic practitioner matching recommendation model for selection of medical practitioners, a dynamic treatment plan generation model for generating a treatment plan, and a dynamic manufacturer selection model for selection of 3d-printed medical appliance manufacturers. The patient system 106 receives information on selected medical practitioners, a generated treatment plan, selected manufacturers, and an advertisement consent request. The medical practitioner system 108 receives information on a patient record, treatment conditions, a generated treatment plan, and a selected manufacturer, and sends a request for generating a treatment plan, selection of a manufacturer, and a request for manufacturing 3D-printed medical appliances. The patient-specific 3D medical appliance manufacturer system 110 manufactures 3D-printed medical appliances based on received requests. The advertisement broker system 112 generates a dynamic advertisement selection model and provides advertisement images selected based on the dynamic advertisement selection model on an advertisement media selected based on the dynamic advertisement selection model.

Advantageously, a system for providing medical treatment based on patient-specific 3D-printed medical appliance using dynamic machine-learning technique is capable of providing a dynamic machine-learning-based practitioner selection, treatment planning, manufacturer selection, and advertisement selection. The computer-based machine learning technology enables more accurate and more effective outputs useful for patients and medical practitioners.

Figure 2:
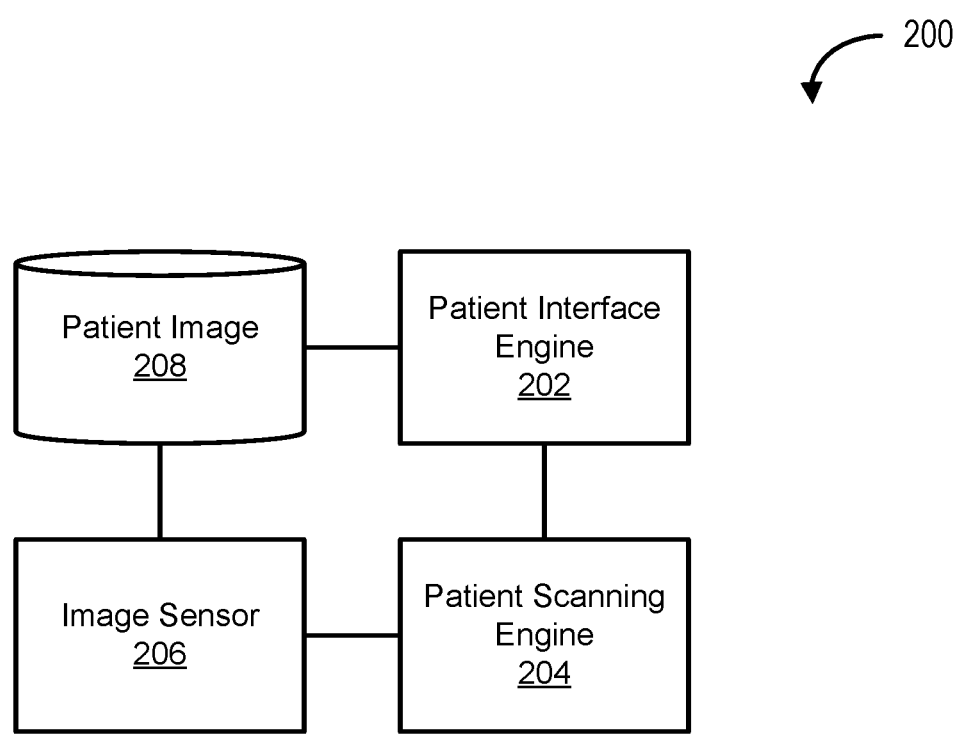
FIG. 2 is a block diagram of an example of a patient system included in a system for providing medical treatment that includes a 3D-printed medical appliance.

FIG. 2 is a block diagram 200 of an example of a patient system included in a system for providing medical treatment that includes a 3D-printed medical appliance. The diagram 200 includes a patient interface engine 202, a patient scanning engine 204 coupled to the patient interface engine 202, an image sensor 206 coupled to the patient scanning engine 204, and a patient image datastore 208 coupled to the image sensor 206 and the patient interface engine 202. In a specific implementation, the patient system depicted in FIG. 2 corresponds to the patient system 106 in FIG. 1.

The patient interface engine 202 is intended to represent hardware configured to interface with a patient to obtain selections, feedback, consent, patient information, and the like, and to communicate with external systems, such as a dynamic 3D-printed medical appliance treatment system, a medical practitioner system, a patient-specific 3D medical appliance manufacturer system, and an advertisement broker system. In a specific implementation, the patient interface engine 202 receives information on one or more potential practitioner candidates matched with a patient by a dynamic 3D-printed medical appliance treatment system, and presents the received information to prompt a patient to make a selection. In a specific implementation, the patient interface engine 202 receives information on a medical practitioner matched with a patient through auction from a dynamic 3D-printed medical appliance treatment system, and presents the received information to prompt a patient to provide consent. In a specific implementation, the patient interface engine 202 receives a medical treatment plan from a dynamic 3D-printed medical appliance treatment system or a medical practitioner system, and presents the medical treatment plan to prompt a patient for review. In a specific implementation, the patient interface engine 202 receives information on one or more potential 3D-printed medical appliance manufacturers, and present the information to prompt a patient to make a selection.

The patient scanning engine 204 is intended to represent hardware configured to generate patient image data of a patient's body part (e.g., oral part, head part, etc.) scanned by an image sensor 206. Depending upon implementation-specific or other considerations, the image data may be 2D image data or 3D image data. When 3D image data is generated, the patient scanning engine 204 may include a specifically manufactured 3D image processing module including depth map calculation function, or a 2D image processing module with additional functional module for 3D imaging. Depending upon implementation- or configuration-specific factors, 3D images or some other component in addition to 2D images may be required because 2D images or 2D images alone may be deemed to provide insufficient data to print an appliance that is suitable for a particular application, such as a retainer that fits properly in a patient's mouth. For example, an in-home kit for an aligner might include an impression kit that is mailed, in addition to 2D images a patient uploads, both of which must be considered before an aligner or set of aligners is delivered to the patient (when they come in, via mail, or in some other applicable manner). In contrast, for same day aligners, 3D images scanned in-office, without an impression kit, are adequate in accordance with techniques described in this paper.

The image sensor 206 is intended to represent hardware (e.g., a camera) configured to capture 2D and/or 3D patient body part images. In a specific implementation, the image sensor 206 includes various applicable image sensors such as CCD image sensors and CMOS image sensors. In a specific implementation, the image sensor 206 is formed in a shape to fit to an intended patient's body part. For example, the image sensor 206 may be formed to be accommodated in a patient's mouth when tooth arrangement for orthodontic treatment is obtained from the image data.

The patient image datastore 208 is intended to represent a datastore to store one or more patient body part images captured by the image sensor 206. In a specific implementation, an entry of the patient image table includes an identification of objects within a patient body part image, an identification of a patient, parameter values associated with the patient image table, and stored location information of the objects within a patient body part image.

In a specific implementation, patients are shown an outcome of treatment without ever getting a practitioner involved. In such an implementation, patients can get started right away with a first device set and a practitioner can do the rest of the workflow later, remotely. The intelligence behind such a system could be powered by machine learning to improve efficiency and outcomes. Also, components of a medical practitioner system, such as is described with reference to FIG. 3, can be automated and implemented on a patient device, on a platform (e.g., in the cloud), or in some other manner that provides the patient access to the relevant expert system. Similarly, components of a patient-specific 3D medical appliance manufacturer system, such as is described with reference to FIG. 4, can be automated or physically implemented by or on behalf of the patient.

In an example of operation of the system shown by way of example in FIG. 2, the patient interface engine 202 receives an instruction from a patient to capture an image. The patient scanning engine 204 functions to scan the relevant parts of a patient, such as the mouth. The image sensor 206 captures 2D and/or 3D patient body part images, such as images of the teeth and gums. The patient image datastore 208 stores patient body part images. The patient interface engine 202 then provides a relevant one or more of the images to some other party.

Figure 3:
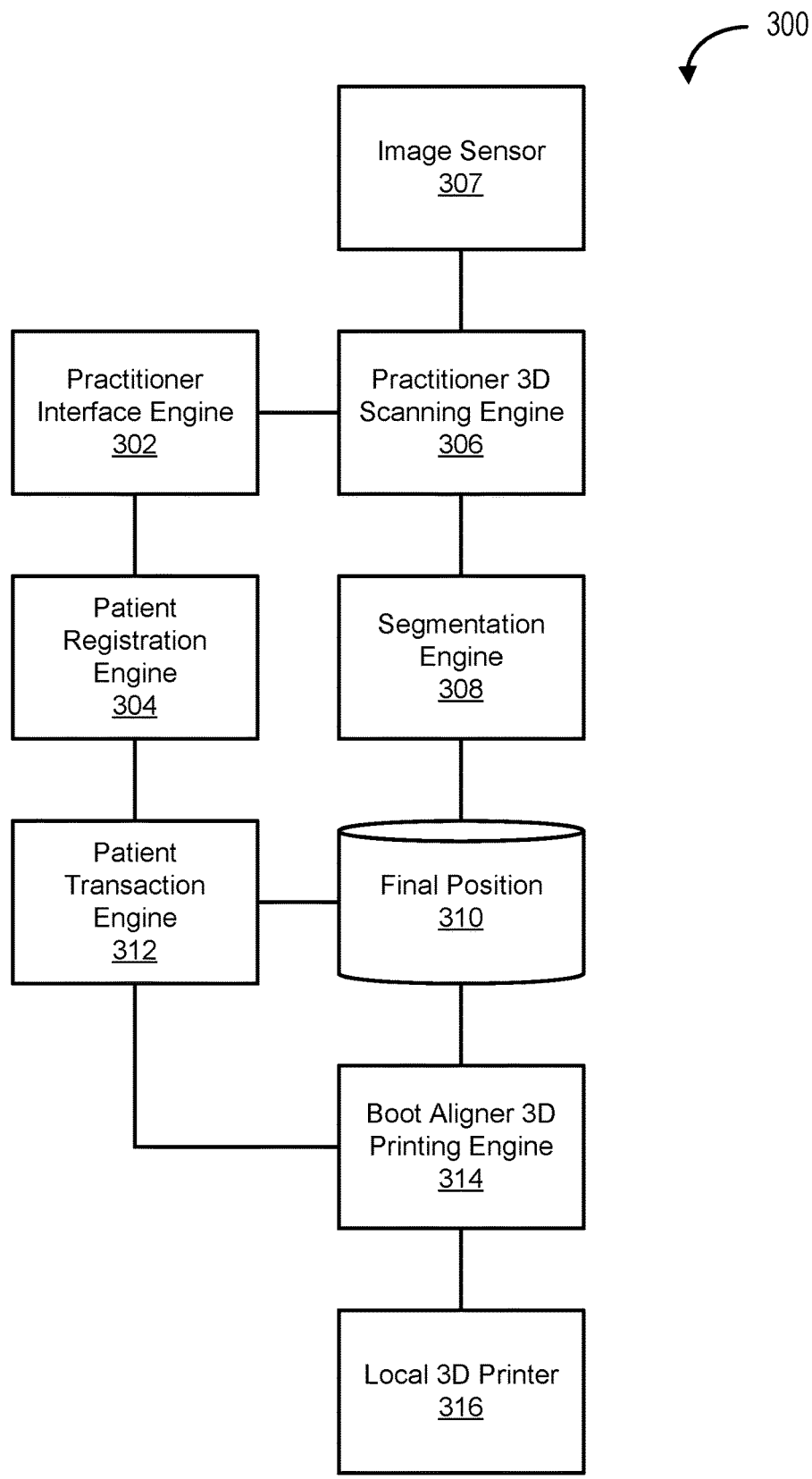
FIG. 3 is a block diagram of an example of a medical practitioner system included in a system for providing medical treatment that includes a 3D-printed medical appliances.

FIG. 3 is a block diagram 300 of an example of a medical practitioner system included in a system for providing medical treatment that includes a 3D-printed medical appliances. The diagram 300 includes a practitioner interface engine 302, a patient registration engine 304 coupled to the practitioner interface engine 302, a practitioner 3D scanning engine 306 coupled to the practitioner interface engine 302, an image sensor 307 coupled to the practitioner 3D scanning engine 306, a segmentation engine 308 coupled to the practitioner 3D scanning engine 306, a final position datastore 310 coupled to the segmentation engine 308, a patient transaction engine 312 coupled to the patient registration engine 304 and the final position datastore 310, a boot aligner 3D printing engine 314 coupled to the patient transaction engine 312 and the final position datastore 310, and a local 3D printer 316 coupled to the boot aligner 3D printing engine 314. In a specific implementation, the medical practitioner system depicted in FIG. 3 corresponds to the medical practitioner system 108 in FIG. 1.

The practitioner interface engine 302 is intended to represent hardware configured to interface with a medical practitioner.

The patient registration engine 304 is intended to represent hardware configured to register a patient who is going to receive a 3D-printed medical appliance based treatment. In a specific implementation, upon registration of the patient, a patient record, which include patient attributes (e.g., age, gender, race, residence, etc.), is generated. The record includes one or more patient body part images (e.g., images of teeth and gums), which can be obtained from a patient system. Practitioners, such as dentists, frequently have multiple chairs and operatories. At many points, there are vacancies and there is excess capacity in offices, both in terms of space and staff time. Advantageously, because the patient has some control over the treatment process as described previously in this paper, demand for services can be matched with supply in the form of space and staff bandwidth. Excess capacity can be used for a variety of related services, such as scanning, progress checking, emergencies, etc.

The practitioner 3D scanning engine 306 is intended to represent hardware configured to generate patient 3D image data of the patient's body part based on image data of patient's body part (e.g., oral part, head part, etc.) scanned by the image sensor 307. In a specific implementation, in generating patient 3D image data, the practitioner 3D scanning engine 306 may include a specifically manufactured 3D image processing module including depth map calculation function, or a 2D image processing module with additional functional module for 3D imaging.

The segmentation engine 308 is intended to represent hardware configured to perform segmentation of a patient's body state based on patient 3D image data of the patient. In a specific implementation, the segmentation includes identification of patient's body objects or sub-parts within the patient's body part based on the patient 3D image data of the patient, and determine locations of the identified sub-parts. For example, segmentation can include identifying individual teeth in one or more images of teeth and gums.

The final position datastore 310 is intended to represent a datastore to store final position data. Final position data can be determined from an aesthetic preference of a medical practitioner as applied to image objects, a likely success rate of such a treatment, or other considerations, and can be tailored based on a practitioner's experience and skill level data and based on past outcomes delivered by the practitioner or other similarly-situated professionals. For example, a dentist may have an aesthetic preference for teeth placement, which can be represented using the tooth objects oriented to match the final position, as well as an aesthetic preference for the overall face/head.

The patient transaction engine 312 is intended to represent hardware configured to enable a patient to purchase a 3D-printed medical appliance based medical treatment. In a specific implementation, the transaction includes a contract between a patient and a medical practitioner, and payment for the 3D-printed medical appliance based medical treatment. In an alternative, subscription payments, payments using digital currencies, payment in exchange for other services, or the like are used.

The boot aligner 3D printing engine 314 is intended to represent hardware configured to generate 3D printer data for a boot 3D-printed medical appliance based on patient 3D image data. In a specific implementation, the 3D printer data for the boot 3D-printed medical appliance includes a plurality of layers of 2D image data suited for 3D printing. The boot 3D-printed medical appliance may or may not result in an appliance that causes body parts (e.g., teeth) to move from a first position to a second position. Trial 3D-printed medical appliances can be provided to enable a patient to get used to wearing the appliance.

The local 3D printer 316 is intended to represent hardware configured to produce a boot 3D-printed medical appliance based on the patient 3D image data generated by the boot aligner 3D by the boot aligner 3D printing engine 314. Depending upon implementation- and/or configuration-specific factors, the boot 3D-printed medical appliance can be implemented as a trial 3D-printed medical appliance, a starter 3D-printed medical appliance, or a reboot 3D-printed medical appliance.

In an example of operation of the system shown by way of example in FIG. 3, the practitioner interface engine 302 functions to interface with a medical practitioner. The patient registration engine 304 registers patients and generates patient records. The practitioner 3D scanning engine 306 generates 3D scanning data of a patient body part, based on 2D and/or 3D image data that have been obtained. The segmentation engine 308 performs segmentation of a patient's body part based on 3D scanning data of the patient body part. The final position datastore 310 stores the final position data for a body part that is to be moved. The patient transaction engine 312 facilitates payment for a 3D-printed medical appliance based dental treatment. The boot aligner 3D printing engine 314 generates 3D printer data for a boot 3D-printed medical appliance based on the 3D scanning data of a patient body part. The local 3D printer 316 produces a boot 3D-printed medical appliance based on the 3D printer data generated by the boot aligner 3D printing engine 314.

Figure 4:
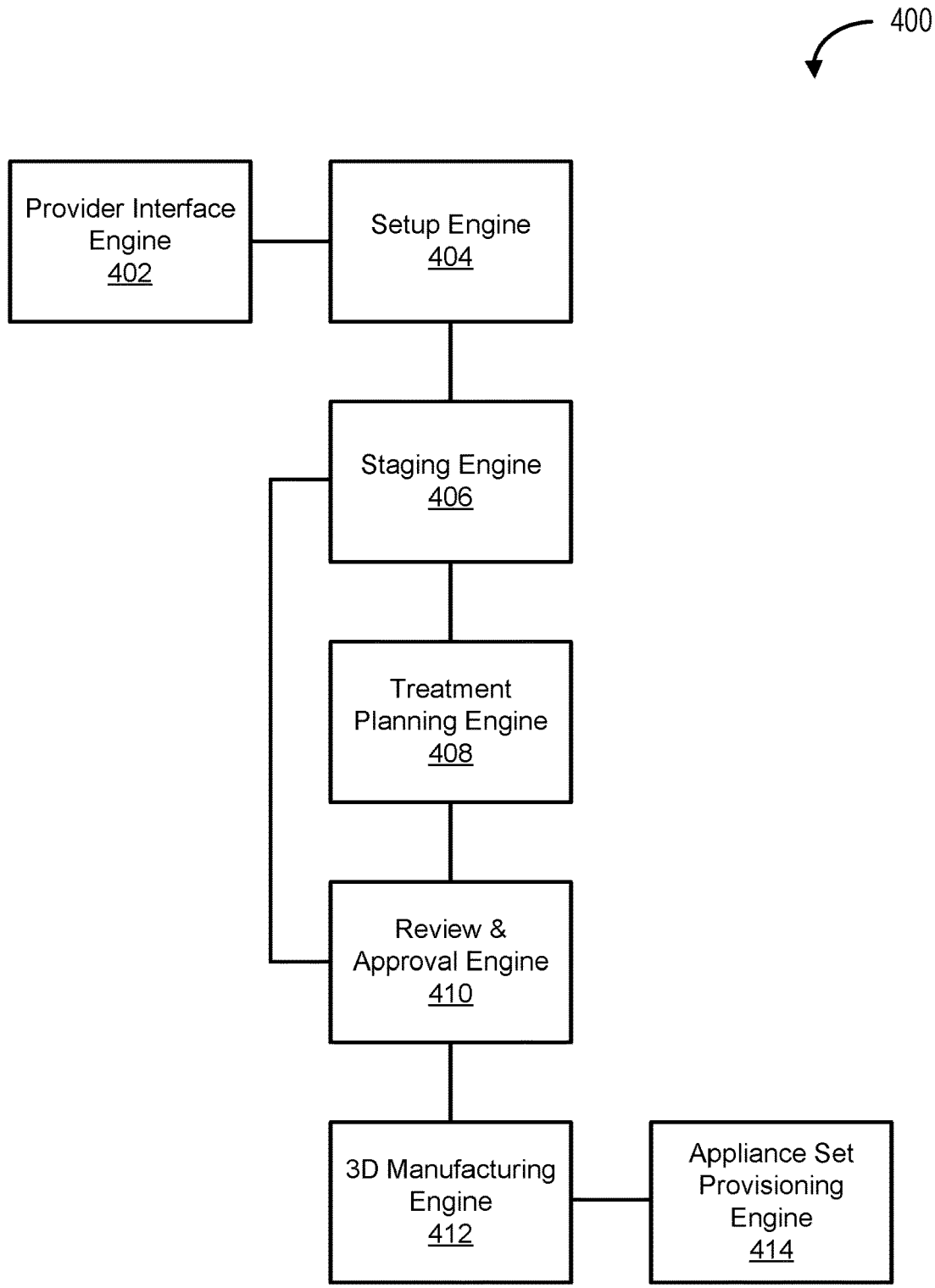
FIG. 4 is a block diagram of an example of a patient-specific 3D medical appliance manufacturer system included in a system for providing medical treatment that includes a 3D-printed medical appliance.

FIG. 4 is a block diagram 400 of an example of a patient-specific 3D medical appliance manufacturer system included in a system for providing medical treatment that includes a 3D-printed medical appliance. The diagram 400 includes a provider interface engine 402, a setup engine 404 coupled to the provider interface engine 402, a staging engine 406 coupled to the setup engine 404, a treatment planning engine 408 coupled to the staging engine 406, a review & approval engine 410 coupled to the staging engine 406 and the treatment planning engine 408, a 3D manufacturing engine 412 coupled to the review & approval engine 410, and an appliance set provisioning engine 414 coupled to the 3D manufacturing engine 412. In a specific implementation, the patient-specific 3D medical appliance manufacturer system depicted in FIG. 4 corresponds to the patient-specific 3D medical appliance manufacturer system 110 in FIG. 1.

The provider interface engine 402 is intended to represent hardware configured to interface with a service provider and other systems from which a patient record, which includes 3D scanning data and presents the received patient record to a service provider for review. For example, the provider interface engine 402 presents a pre-treatment state (e.g., 3D scanning data) and/or an expected post-treatment state (e.g., final position data), for review. In a specific implementation, the provider interface engine 402 receives a request to generate a 3D-printed medical appliance based treatment plan based on the pre-treatment state represented by 3D scanning data and the pre-treatment state represented by the final position data.

The setup engine 404 is intended to represent hardware configured to set up a 3D-printed medical appliance based medical treatment. In setting up a 3D-printed medical appliance based dental treatment, the setup engine 404 retrieves a patient record including the 3D scanning data and the final position data. In a specific implementation, the set-up 3D-printed medical appliance based medical treatment is associated with a specific patient and a specific medical practitioner, and managed in association with a patient record of the patient and a medical practitioner record of the medical practitioner. The setup engine 404 can generate multiple setups for a single patient. For example, one version can show corrected front teeth and another can show all teeth corrected. Every such setup has time, cost, and success rate implications. Practitioners can choose to share some or all versions with a patient to allow the patient to choose.

The staging engine 406 is intended to represent hardware configured to determine treatment conditions of a 3D-printed medical appliance based dental treatment, based on a patient record and inputs by the patient. In a specific implementation, the treatment conditions may include a budget range, a treatment duration, a pre-and post-treatment state (e.g., post-treatment tooth arrangement), an acceptable pain level, and so on. Staging entails deciding configurations for appliances from a first appliance, which moves body parts from an original position, to a last appliance, which moves body parts to a final position.

The treatment planning engine 408 is intended to represent hardware configured to generate a treatment plan based on a patient record and treatment conditions. In a specific implementation, a treatment plan may include an expected pre-and post-treatment state of the patient's body part, a treatment term (e.g., length of time and phases), expected pain levels, an estimated price, (e.g., final position data), transitioning states of the patient's body part, a treatment term (e.g., length of time and phases), types and designs of 3D-printed medical appliances to be used for each of different phases of the treatment, and manner and duration of attaching 3D-printed medical appliances, and so on. For example, a 3D animation to show transition from a pre-treatment state to a post-treatment state may be generated.

The review & approval engine 410 is intended to represent hardware configured to provide a treatment plan to a patient and/or a medical practitioner and receive approval of the treatment plan therefrom. In a specific implementation, the engines 406, 408, 410 loop until a treatment plan is approved.

The 3D manufacturing engine 412 is intended to represent hardware configured to generate 3D data for a set of 3D-medical appliances based on a patient 3D image data, a treatment plan, and a final position. In a specific implementation, the 3D data for the set of 3D-medical appliances includes a plurality of layers of 2D image data suited for 3D printing. Alternatively, the 3D medical appliances can be manufactured in a known or convenient manner.

The appliance set provisioning engine 414 is intended to represent hardware configured to prepare a set of 3D medical appliances, such as aligners, for delivery to a patient. The hardware can print all appliances for a case or print in batches over time. With batch processing, the patient may repeat a scan, which may or may not entail meeting with a practitioner or other party capable of scanning. Batch sizes can be customized based on patient info, with larger batches being more appropriate for easier cases or in accordance with preferences. Based on difficult movements in a case, patients can be given recommendations to take a scan at specific points in their treatment, with batch sizes potentially correlated to the duration between the specific points. In a specific implementation, scans happen remotely and appliances are shipped to the patient. The repeated scan facilitates comparison between actual progress and progress predicted in association with a plan, enabling appliance manufacturers to respond to actual progress instead of, potentially inaccurate, predicted progress. Because of the value of this dynamic, self-correcting loop, it may continue to exist even following advancements in 3D printing and improvements in treatment plans through advanced machine learning techniques, not replacing printing everything all at-once in the foreseeable future, though it is likely to replace in some instances. Delivery can be accomplished by handing appliances to a patient in person, over the mail, or in some other applicable manner.

In an example of operation of the system shown by way of example in FIG. 4, the provider interface engine 402 functions to receive patient information. The setup engine 404 sets up a 3D medical appliance treatment. Until approval is obtained, the staging engine 406 determines treatment conditions of a 3D medical appliance treatment; the treatment planning engine 408 provides a treatment plan, and the review & approval engine 410 obtains approval for the treatment plan. The 3D manufacturing engine 412 generates 3D data for a set of 3D medical treatment appliances based on patient 3D image data. The appliance set provisioning engine 414 prepares for delivery of a set of 3D medical treatment appliances based on the 3D data generated by the 3D manufacturing engine 412.

Figure 5:
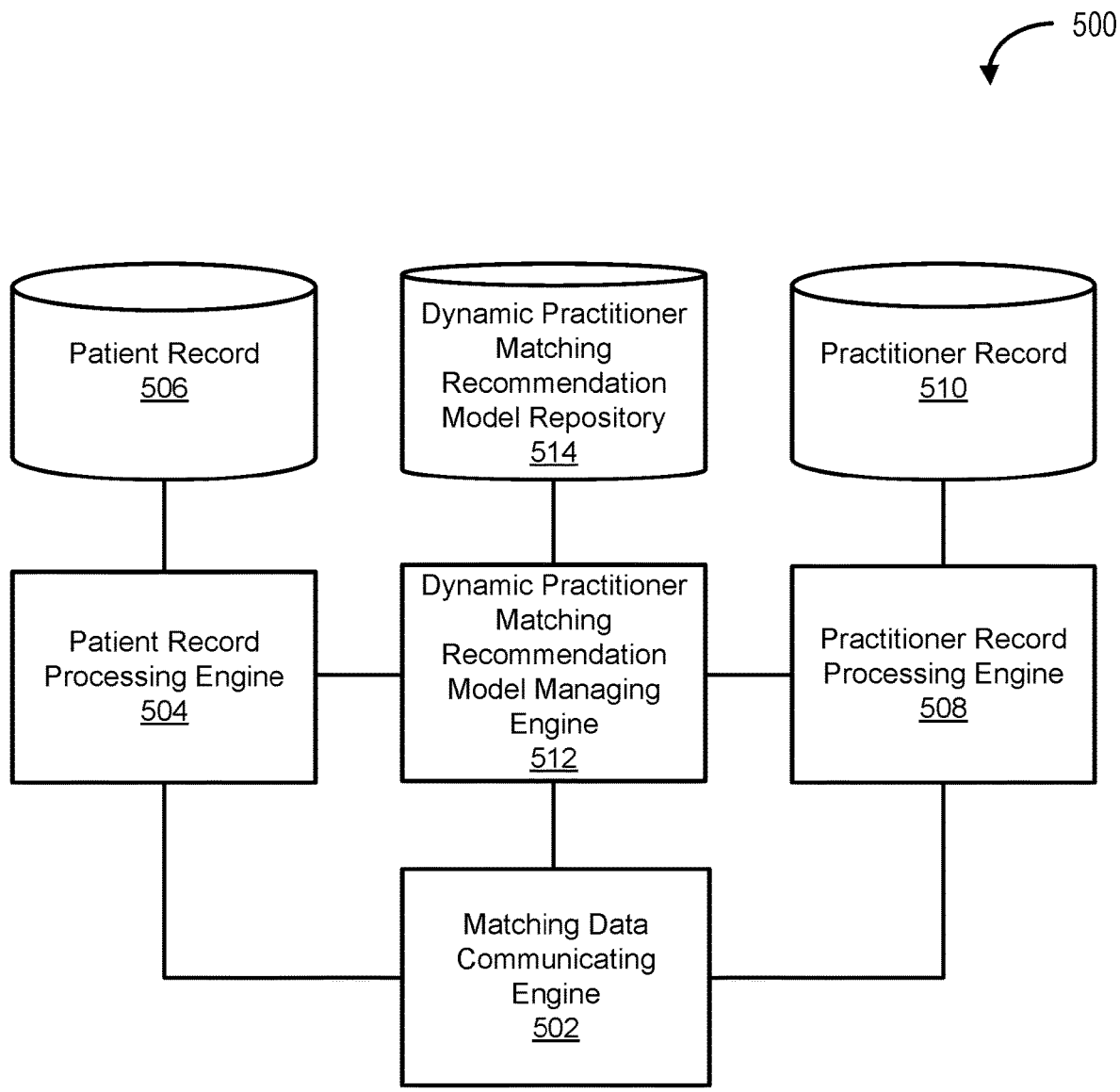
FIG. 5 is a block diagram of an example of a dynamic 3D-printed medical appliance treatment system for providing a practitioner matching recommendation service.

FIG. 5 is a block diagram 500 of an example of a dynamic 3D-printed medical appliance treatment system for providing a practitioner matching recommendation service. The example architecture shown in FIG. 5 includes a matching data communicating engine 502, a patient record processing engine 504 coupled to the matching data communicating engine 502, a patient record datastore 506 coupled to the patient record processing engine 504, a practitioner record processing engine 508 coupled to the matching data communicating engine 502, practitioner record datastore 510 coupled to the practitioner record processing engine 508, a dynamic practitioner matching recommendation model managing engine 512 coupled to the matching data communicating engine 502, the patient record processing engine 504, and the practitioner record processing engine 508, and dynamic practitioner matching recommendation model datastore 514 coupled to the dynamic practitioner matching recommendation model managing engine 512. In a specific implementation, the dynamic 3D-printed medical appliance treatment system depicted in FIG. 5 corresponds to the dynamic 3D-printed medical appliance treatment system 104 in FIG. 1.

The matching data communicating engine 502 is intended to represent hardware configured to communicate with a patient system and a medical practitioner system. In a specific implementation, in communicating with a patient system, the matching data communicating engine 502 receives patient information used to generate a patient record. Depending upon implementation-specific or other considerations, patient information may include patient attributes (e.g., age, gender, race, residence, etc.) of a patient and information on a pre-treatment state (e.g., pre-treatment tooth arrangement) of a patient. In a specific implementation, in communicating with a medical practitioner system, the matching data communicating engine 502 receives practitioner information used to generate a practitioner record. Depending upon implementation-specific or other considerations, practitioner information may include a geographical location, schedules, practice field, price range, and rating of a medical practitioner.

In a specific implementation, the matching data communicating engine 502 is also configured to provide, to a patient system, information on potential practitioner candidates that are selected through medical practitioner matching and receive user selection inputs of one of the potential practitioner candidates from a patient system. Further, in a specific implementation, upon receiving user selection inputs, the matching data communicating engine 502 provides a patient record and treatment conditions to a medical practitioner system of the selected medical practitioner by the user selection inputs.

The patient record processing engine 504 is intended to represent hardware configured to generate a patient record based on patient information obtained through the matching data communicating engine 502. In a specific implementation, the patient record includes information included in the patient information and also self-captured 2D pictures of a patient body part (e.g., teeth), which are sent from also a patient system, and may or may not include detailed 3D scanning data. In a specific implementation, the patient record includes patient preferences on treatment, such as a geographical location, a budget range, pain levels throughout the treatment, a treatment term (e.g., time length), a post-treatment state, and so on.

The patient record datastore 506 is intended to represent a datastore of one or more patient records generated by the patient record processing engine 504. In a specific implementation, in storing one or more patient records, the patient record datastore 506 manages the stored patient records using a patient record table including a plurality of entries each of which corresponds to a patient record. For example, an entry of the patient record table includes an identification of the patient record, an identification of a patient, parameter values associated with the patient table, and stored location information of the patient record. In a specific implementation, in storing one or more patient records, the patient record datastore 506 also stores a machine learning model applicable to one or more patient records stored therein.

The practitioner record processing engine 508 is intended to represent hardware configured to generate a practitioner record based on medical practitioner information obtained through the matching data communicating engine 502. In a specific implementation, the practitioner record includes information included in the practitioner information such as a geographical location, schedules, practice field, price range, and rating of a medical practitioner.

The practitioner record datastore 510 is intended to represent a datastore to store one or more practitioner records generated by the practitioner record processing engine 508. In a specific implementation, in storing one or more practitioner records, the practitioner record datastore 510 manages the stored practitioner records in a same or similar manner as the patient record datastore 506 storing the patient records.

The dynamic practitioner matching recommendation model managing engine 512 is intended to represent hardware configured to generate a dynamic medical practitioner matching recommendation model. In a specific implementation, the dynamic medical practitioner matching recommendation model is configured to determine one or more potential practitioner candidates that are considered to match a patient record and preferences. In a specific implementation, the dynamic medical practitioner matching recommendation model may include a plurality of parameters for determining resulting potential practitioner candidates for a specific patient, and parameter values of the parameters may be modified through applicable machine learning techniques. In a specific implementation, the parameters of the dynamic medical practitioner matching recommendation model may include a geographical location of a patient, patient preferences (treatment conditions), and a geographical location, schedules, practice field, price range, and rating of a practitioner.

In a specific implementation, the dynamic practitioner matching recommendation model managing engine 512 is configured to determine potential practitioner candidates by applying a patient record, treatment conditions, and practitioner records to a dynamic medical practitioner matching recommendation model. Depending upon implementation-specific or other considerations, one or more practitioners whose practitioner records match treatment conditions and/or the patient record may be selected as the potential practitioner candidates.

In a specific implementation, the dynamic practitioner matching recommendation model managing engine 512 is configured to provide information on the potential practitioner candidates (e.g., the practitioner records) to a patient system of the patient, such that the patient can select one of the potential practitioner candidates who is going to perform medical treatment of the patient. Further, in a specific implementation, upon selection of one of the potential practitioner candidates by the patient, the dynamic practitioner matching recommendation model managing engine 512 is configured to receive user selection inputs indicating one of the potential practitioner candidates, and provides a patient record and treatment conditions to a practitioner system of the selected practitioner upon reception of the user selection inputs.

In a specific implementation, the dynamic practitioner matching recommendation model managing engine 512 is configured to receive user feedback from a patient system. Depending upon implementation-specific or other considerations, the user feedback may include applicability (e.g., how service conditions provided by practitioner matches patient's treatment conditions), convenience of appointment time, number of appointments, and quality of service (QoS) determined subjectively by the patient. Further, in a specific implementation, the dynamic practitioner matching recommendation model managing engine 512 is configured to modify the dynamic medical practitioner matching recommendation model based on the user feedback. In a specific implementation, the dynamic practitioner matching recommendation model managing engine 512 modifies specific parameter values and/or weighting balance of parameters of the dynamic medical practitioner matching recommendation model, in accordance with an applicable machine learning technique such as a decision tree learning, association rule learning, artificial neural networks, deep learning, etc.

The dynamic practitioner matching recommendation model datastore 514 is intended to represent a datastore to store one or more dynamic medical practitioner matching recommendation models generated by the dynamic practitioner matching recommendation model managing engine 512. In a specific implementation, in storing one or more dynamic medical practitioner matching recommendation models, the dynamic practitioner matching recommendation model datastore 514 manages the stored dynamic medical practitioner matching recommendation models in a same or similar manner as the patient record datastore 506 storing the patient records and/or the practitioner record datastore 510 storing the practitioner records.

In an example of operation of the system shown by way of example in FIG. 5, the matching data communicating engine 502 communicates with a patient system to obtain patient information to generate a patient record, and with a medical practitioner system to obtain medical practitioner information to generate a practitioner record. The patient record processing engine 504 generates a patient record based on patient information obtained through the matching data communicating engine 502, and stores the generated patient record in the patient record datastore 506. The practitioner record processing engine 508 generates a practitioner record based on medical practitioner information obtained through the matching data communicating engine 502, and stores the generated practitioner record in the practitioner record datastore 510. The dynamic practitioner matching recommendation model managing engine 512 generates a dynamic medical practitioner matching recommendation model and stores the generated dynamic medical practitioner matching recommendation model in the dynamic practitioner matching recommendation model datastore 514.

Further, in an example of operation of the system shown by way of example in FIG. 5, the dynamic practitioner matching recommendation model managing engine 512 determines treatment conditions based on a patient record, obtains practitioner records, and determines potential practitioner candidates using the dynamic medical practitioner matching recommendation model. The dynamic practitioner matching recommendation model managing engine 512 receives user selection inputs to select one of the potential practitioner candidates, provides a patient record and treatment conditions to a practitioner system of the selected practitioner. The dynamic practitioner matching recommendation model managing engine 512 receives user feedback from a patient system, and modifies the dynamic medical practitioner matching recommendation model based on the user feedback.

Figure 6:
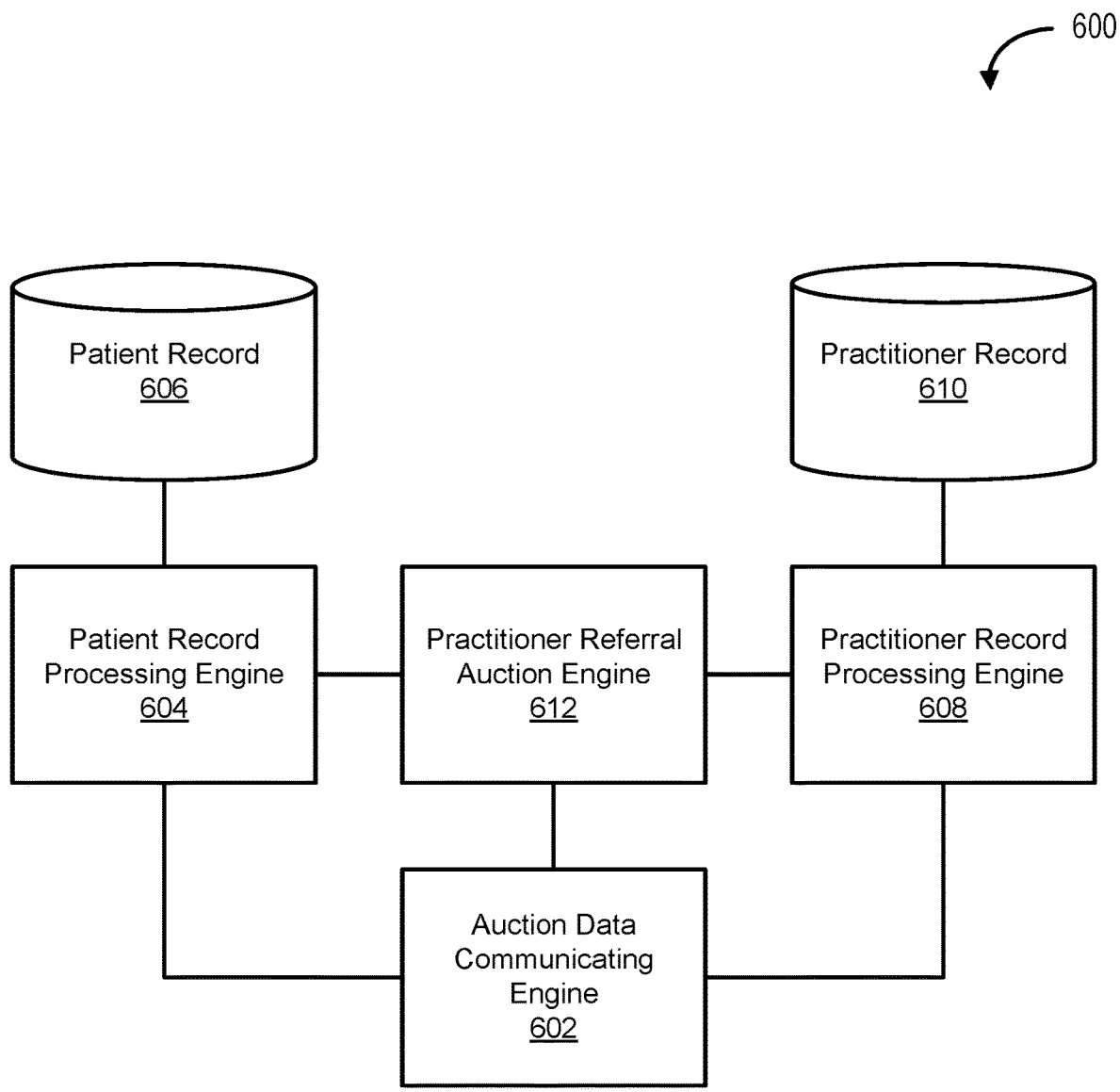
FIG. 6 is a block diagram of an example of a dynamic 3D-printed medical appliance treatment system for providing a practitioner referral auction service.

FIG. 6 is a block diagram 600 of an example of a dynamic 3D-printed medical appliance treatment system for providing a practitioner referral auction service. The example of the dynamic 3D-printed medical appliance treatment system shown in FIG. 6 includes an auction data communicating engine 602, a patient record processing engine 604 coupled to the auction data communicating engine 602, patient record datastore 606 coupled to the patient record processing engine 604, a practitioner record processing engine 608 coupled to the auction data communicating engine 602, practitioner record datastore 610 coupled to the practitioner record processing engine 608, a practitioner referral auction engine 612 coupled to the auction data communicating engine 602, the patient record processing engine 604, and the practitioner record processing engine 608. In a specific implementation, the dynamic 3D-printed medical appliance treatment system depicted in FIG. 6 corresponds to the dynamic 3D-printed medical appliance treatment system 104 in FIG. 1 and/or the dynamic 3D-printed medical appliance treatment system in FIG. 5.

In a specific implementation, the auction data communicating engine 602, the patient record processing engine 604, the patient record datastore 606, the practitioner record processing engine 608, and the practitioner record datastore 610 function in the same or similar manner as the matching data communicating engine 502, the patient record processing engine 504, the patient record datastore 506, the practitioner record processing engine 508, and the practitioner record datastore 510 in FIG. 5.

The practitioner referral auction engine 612 is intended to represent hardware configured to generate and manage a medical practitioner referral auction instance for selecting a medical practitioner to whom a patient record is provided based on auction. Depending upon implementation-specific or other considerations, the medical practitioner referral auction instance is a computer program configured to select one or more potential practitioner candidates to whom invitation to a medical practitioner referral auction is provided based on a patient record, patient's preference (treatment condition), and practitioner records of registered medical practitioners. In a specific implementation, the medical practitioner referral auction instance may be executed based on a plurality of parameters for determining potential practitioner candidates for a specific patient, and parameter values of the parameters may be modified through applicable machine learning techniques. In an alternative, rather than auction, a fixed pricing model can be used to consider patient parameters from practitioner records, treatment conditions, and patient records. In such an implementation, FIG. 6 can be modified to replace "auction" with "fixed pricing model."

In a specific implementation, the practitioner referral auction engine 612 is configured to determine treatment conditions based on a patient record obtained from the patient record datastore 606, and obtain practitioner records of registered medical practitioner from the practitioner record datastore 610. Further, in a specific implementation, the practitioner referral auction engine 612 is configured to select one or more potential practitioner candidates based on practitioner records, the treatment conditions, and the patient record. Further, upon selecting the one or more potential practitioner candidates, the practitioner referral auction engine 612 is configured to provide auction data (e.g., invitation to a medical practitioner referral auction) to medical practitioner systems of the potential practitioner candidates. In a specific implementation, auction data include a generic version of a patient record and information about an auction procedure (e.g., limits on bid number, deadline, etc.), information about referral fee for the service, and so on.

In a specific implementation, the practitioner referral auction engine 612 is configured to provide auction data (e.g., invitation to a medical practitioner referral auction) to a medical practitioner systems of the potential practitioner candidates. In a specific implementation, auction data include a generic version of a patient record and/or treatment conditions and information about an auction procedure (e.g., limits on bid number, deadline, etc.), information about referral fee for the service, and so on. In a specific implementation, the practitioner referral auction engine 612 is configured to receive bids from medical practitioner systems of one or more of the potential practitioner candidates. In a specific implementation, a bid includes an agreed fee amount input by a medical practitioner. In a specific implementation, the practitioner referral auction engine 612 is configured to select one winning practitioner based on the bid amount (or the adjusted bid amount) or other applicable criteria. In a specific implementation, the practitioner referral auction engine 612 is configured to send a complete version of a patient record and/or treatment conditions to a medical practitioner system of the winning practitioner. In a specific implementation, upon a patient's consent to use the winning practitioner, the practitioner referral auction engine 612 sends the patient record and/or treatment conditions.

In an example of operation of the example system shown in FIG. 6, the auction data communicating engine 602 communicates with a patient system to obtain patient information to generate a patient record, and with a medical practitioner system to obtain medical practitioner information to generate a practitioner record. The patient record processing engine 604 generates a patient record based on patient information obtained through the matching data communicating engine 602, and stores the generated patient record in the patient record datastore 606. The practitioner record processing engine 608 generates a practitioner record based on medical practitioner information obtained through the auction data communicating engine 602, and stores the generated practitioner record in the practitioner record datastore 610. The practitioner referral auction engine 612 generates a medical practitioner referral auction instance and functions to perform medical practitioner referral auction in the medical practitioner referral auction instance.

Figure 7:
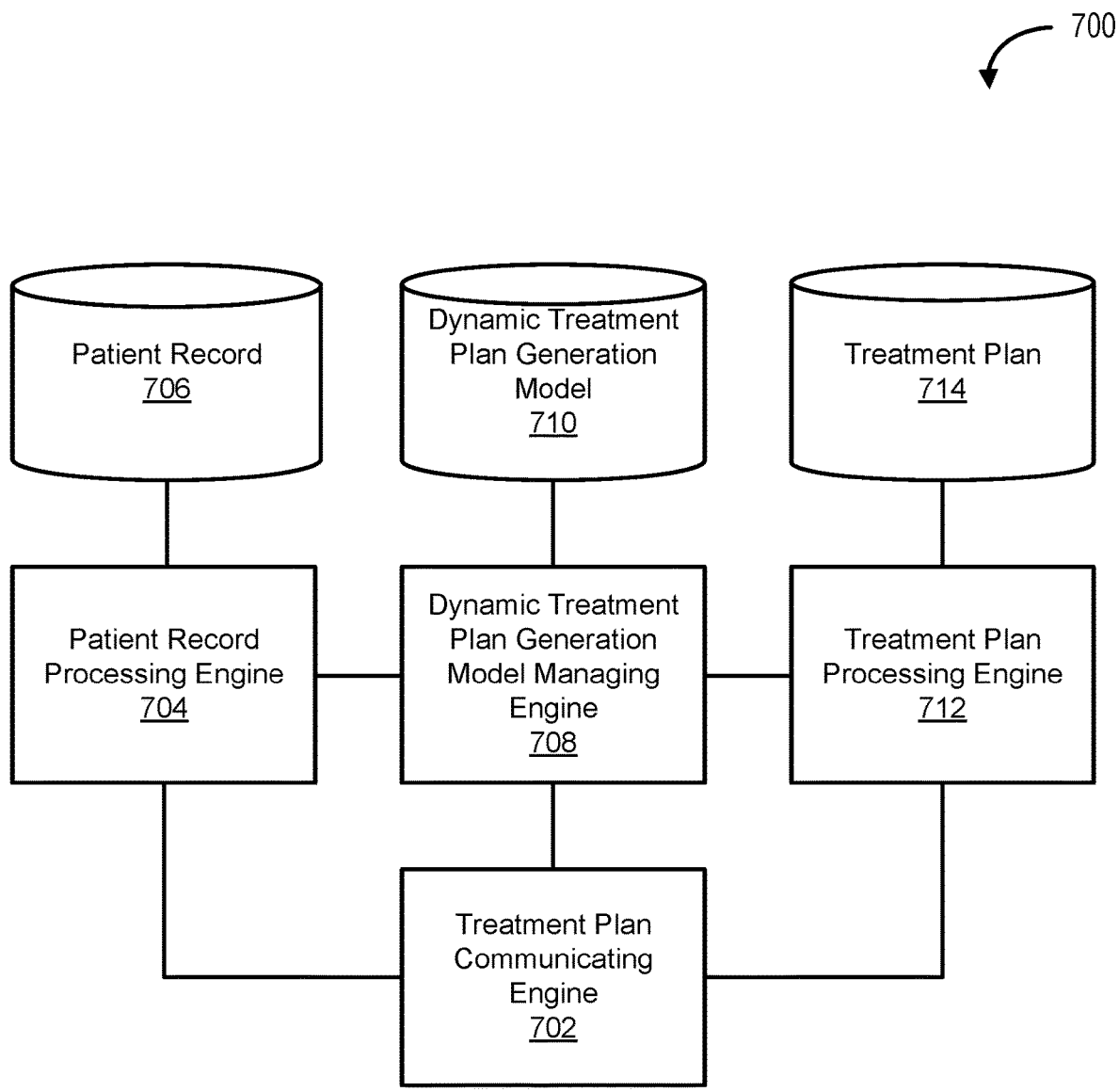
FIG. 7 is a block diagram of an example of a dynamic 3D-printed medical appliance treatment system for providing a 3D medical appliance treatment plan.

FIG. 7 is a block diagram 700 of an example of a dynamic 3D-printed medical appliance treatment system for providing a 3D medical appliance treatment plan. The example of the dynamic 3D-printed medical appliance treatment system shown in FIG. 7 includes a treatment plan communicating engine 702, a patient record processing engine 704 coupled to the treatment plan communicating engine 702, patient record datastore 706 coupled to the patient record processing engine 704, a dynamic treatment plan generation model managing engine 708 coupled to the treatment plan communicating engine 702 and the patient record processing engine 704, a dynamic treatment plan generation model datastore 710 coupled to the dynamic treatment plan generation model managing engine 708, a treatment plan processing engine 712 coupled to the treatment plan communicating engine 702 and the dynamic treatment plan generation model managing engine 708, and a treatment plan datastore 714 coupled to the treatment plan processing engine 712. In a specific implementation, the dynamic 3D-printed medical appliance treatment system depicted in FIG. 7 corresponds to the dynamic 3D-printed medical appliance treatment system in FIGS. 1, 5, and/or 6.

The treatment plan communicating engine 702 is intended to represent hardware configured to communicate with a patient system, a medical practitioner system, and a patient-specific 3D medical appliance manufacturer system. In a specific implementation, the treatment plan communicating engine 702 is configured to communicate with a patient system to obtain patient information. In a specific implementation, the treatment plan communicating engine 702 is configured to communicate with a medical practitioner system to receive a request to generate a medical treatment plan based on a patient record and treatment conditions. In a specific implementation, the treatment plan communicating engine 702 is configured to communicate with a 3D medical appliance manufacturer system to send a request for manufacturing a set of patient-specific 3D medical appliances.

Advantageously, the treatment plan communicating engine 702 can be implemented as part of or in conjunction with a practice management system in a dental office, including practice management systems, including practice management systems already implemented in an office to manage patient scheduling prior to incorporating techniques described in this paper. Other engines, such as the dynamic treatment plan generation model managing engine 708 and the treatment plan processing engine 712, described later, can run in the background and can, for example, create treatment plans for relevant patients asynchronously for Doctor presentation at the time of appointment and for sharing before or after. This can be used as a conversion tool for patients because the patients can be shown what is possible with the use of a treatment plan.

In a specific implementation, the patient record processing engine 704 and the patient record datastore 706 function in the same or similar manner as the patient record processing engine 504 and the patient record datastore 506 in FIG. 5, respectively.

The dynamic treatment plan generation model managing engine 708 is intended to represent hardware configured to generate a dynamic 3D medical appliance treatment plan generation model. Depending upon implementation-specific or other considerations, the dynamic 3D medical appliance treatment plan generation model is a computer algorithm configured to determine a 3D medical appliance treatment plan based on a patient record and treatment conditions. In a specific implementation, the dynamic 3D medical appliance treatment plan generation model may include a plurality of parameters for determining the resulting potential practitioner candidates dynamic 3D medical appliance treatment plan for a specific patient, and parameter values of the parameters may be modified through applicable machine learning techniques. In a specific implementation, the parameters of the dynamic 3D medical appliance treatment plan generation model may include a pre-treatment state of a patient, an expected post-treatment state of the patient, a treatment term (e.g., length of time and phases), expected pain levels, a budget range, and so on.

In a specific implementation, the dynamic treatment plan generation model managing engine 708 is configured to receive user feedback from a patient system and/or a medical practitioner system. Depending upon implementation-specific or other considerations, the user feedback may include practitioner applicability (e.g., how service conditions provided by practitioner matches patient's treatment conditions), quality of practitioner service (QoS) determined subjectively by the patient, manufacturer applicability (e.g., how appliance conditions provided by manufacturer matches the treatment plan), quality of manufacturer service (QoS) determined subjectively by the patient and/or the practitioner. Further, in a specific implementation, the dynamic treatment plan generation model managing engine 708 is configured to modify the dynamic 3D medical appliance treatment plan generation model based on the user feedback. In a specific implementation, the dynamic treatment plan generation model managing engine 708 modifies specific parameter values and/or weighting balance of parameters of the dynamic 3D medical appliance treatment plan generation model, in accordance with an applicable machine learning technique such as a decision tree learning, association rule learning, artificial neural networks, deep learning, etc.

The dynamic treatment plan generation model datastore 710 is intended to represent a datastore to store one or more 3D medical appliance treatment plan generation models generated by the dynamic treatment plan generation model managing engine 708. In a specific implementation, in storing one or more 3D medical appliance treatment plan generation models, the dynamic treatment plan generation model datastore 710 manages the stored 3D medical appliance treatment plan generation models in a same or similar manner as the patient record datastore 506 in FIG. 5 storing the patient records.

The treatment plan processing engine 712 is intended to represent hardware configured to generate a 3D medical appliance treatment plan by applying the patient record, including 3D scanning data, and treatment conditions to a dynamic 3D medical applicant treatment plan generation model. In a specific implementation, a 3D appliance treatment plan may include an expected post-treatment state of the patient, a treatment term (e.g., length of time and phases), expected pain levels, an estimated price, types and designs of 3D-printed medical appliances to be used for each of different phases of the treatment, and manner and duration of attaching 3D-printed medical appliances, and so on. For example, types and designs of 3D-printed medical appliances may include materials, color, and -patient-specific shape of the 3D-printed medical appliances. For example, the manner and duration of attaching 3D-printed medical appliances may include acceptable patient's movement or activity during attachment of the 3D-printed medical appliances, and a time range in a day, week, or month during which the 3D-printed medical appliances should be attached.

The treatment plan datastore 714 is intended to represent a datastore to store one or more 3D medical appliance treatment plans generated by the treatment plan processing engine 712. In a specific implementation, in storing one or more 3D medical appliance treatment plans, the treatment plan datastore 714 manages the stored 3D medical appliance treatment plans in a same or similar manner as the patient record datastore 506 in FIG. 5 storing the patient records.

In an example of operation of the example system shown in FIG. 7, the treatment plan communicating engine 702 communicates with a patient system to obtain patient information to generate a patient record, with a medical practitioner system to receive a request to generate a treatment plan, and with a patient-specific 3D medical appliance manufacturer system to send a request to manufacture a set of patient-specific 3D medical appliances. The patient record processing engine 704 generates a patient record based on patient information obtained through the matching data communicating engine 702, and stores the generated patient record in the patient record datastore 706. The dynamic treatment plan generation model managing engine 708 generates a dynamic treatment plan generation model and stores the generated dynamic treatment plan generation model in the dynamic treatment plan generation model datastore 710. The treatment plan processing engine 712 generates a treatment plan by applying a patient record and treatment conditions to a dynamic treatment plan generation model, and stores the generated treatment plan in the treatment plan datastore 714.

Figure 8:
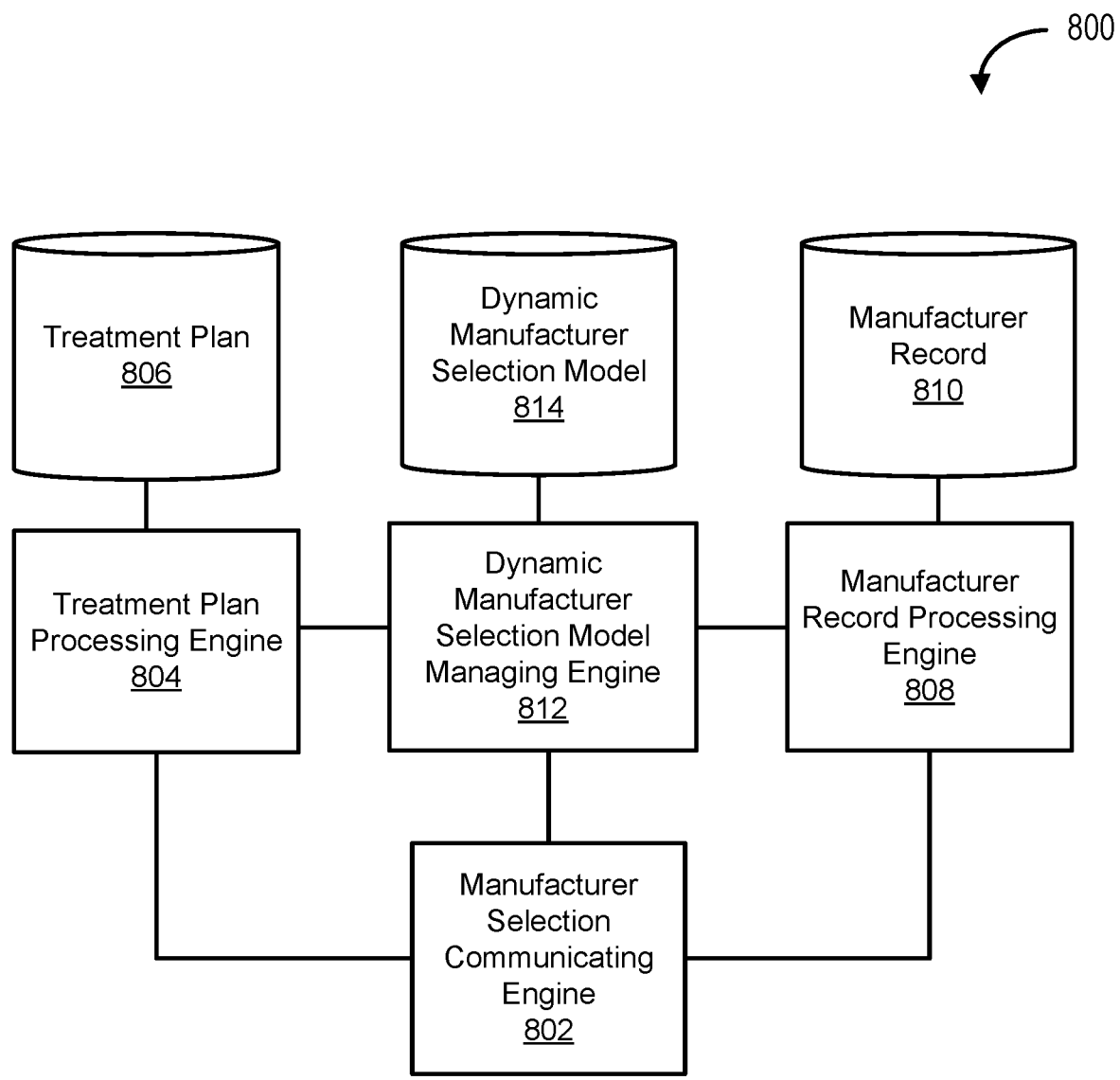
FIG. 8 is a block diagram of an example of a dynamic 3D-printed medical appliance treatment system for providing a 3D medical appliance manufacturer selection service.

FIG. 8 is a block diagram 800 of an example of a dynamic 3D-printed medical appliance treatment system for providing a 3D medical appliance manufacturer selection service. The example of the dynamic 3D-printed medical appliance treatment system shown in FIG. 8 includes a manufacturer selection communicating engine 802, a treatment plan processing engine 804 coupled to the manufacturer selection communicating engine 802, a treatment plan datastore 806 coupled to the treatment plan processing engine 804, a manufacturer record processing engine 808 coupled to the manufacturer selection communicating engine 802, manufacturer record datastore 810 coupled to the manufacturer record processing engine 808, a dynamic manufacturer selection model managing engine 812 coupled to the manufacturer selection communicating engine 802, the treatment plan processing engine 804, and the manufacturer record processing engine 808, and dynamic manufacturer selection model datastore 814 coupled to the dynamic manufacturer selection model managing engine 812. In a specific implementation, the dynamic 3D-printed medical appliance treatment system depicted in FIG. 8 corresponds to the dynamic 3D-printed medical appliance treatment system in FIGS. 1, 5, 6, and/or 7.

The manufacturer selection communicating engine 802 is intended to represent hardware configured to communicate with a patient system, a medical practitioner system, and a 3D medical appliance manufacturer system. In a specific implementation, the manufacturer selection communicating engine 802 is configured to communicate with a 3D medical appliance manufacturer system to obtain manufacturer information. Depending upon implementation-specific or other considerations, manufacturer information may include a geographical location, expected delivery time, manufactured appliance type and design, price range, on-time delivery rating, practitioner's rating, patient's rating, and so on.

In a specific implementation, the manufacturer selection communicating engine 802 is configured to provide information on potential manufacturer candidates that are selected through 3D medical appliance manufacturer selection and receive user selection inputs of one of the potential manufacturer candidates from a patient system or a medical practitioner system. Further, in a specific implementation, upon receiving user selection inputs, the manufacturer selection communicating engine 802 provides a patient record and a treatment plan to a 3D medical appliance manufacturer system of the selected manufacturer by the user selection inputs.

In a specific implementation, the treatment plan processing engine 804 and the treatment plan datastore 806 function in the same or similar manner as the treatment plan processing engine 712 and the treatment plan datastore 714 in FIG. 7, respectively.

The manufacturer record processing engine 808 is intended to represent hardware configured to generate a manufacturer record based on manufacturer information obtained through the manufacturer selection communicating engine 802. In a specific implementation, the manufacturer record includes information included in the manufacturer information such as a geographical location, expected delivery time, manufactured appliance type and design, price range, on-time delivery rating, practitioner's rating, and patient's rating.

The manufacturer record datastore 810 is intended to represent a datastore to store one or more manufacturer records generated by the manufacturer record processing engine 808. In a specific implementation, in storing one or more practitioner records, the manufacturer record datastore 810 manages the stored manufacturer records in a same or similar manner as the treatment plan datastore 806 storing the treatment plans.

The dynamic manufacturer selection model managing engine 812 is intended to represent hardware configured to generate a dynamic manufacturer selection model. Devices for the same patient could be created by the same manufacturer or multiple manufacturers thus allowing for portability of patient's delivery and to align with some specific tools/advantages a manufacturer has on some devices vs. others. This approach facilitates batch printing for the same case and allows consumers to get serviced no matter where they are (e.g. lost my aligners—I am on vacation/away from home).

Depending upon implementation-specific or other considerations, the dynamic manufacturer selection model is configured to determine one or more potential manufacturer candidates that are considered to match a treatment plan based on the treatment plan and manufacturer records. In a specific implementation, the dynamic manufacturer selection model includes a plurality of parameters for determining resulting potential manufacturer candidates for a specific patient, and parameter values of the parameters may be modified through applicable machine learning techniques. In a specific implementation, the parameters of the dynamic manufacturer selection model may include a geographical location of a patient, treatment-plan-specific parameters, such as a treatment term (e.g., length of time and phases), expected pain levels, an estimated price, types and designs of 3D medical appliances to be used for each of different phases of the treatment, and manner and duration of attaching 3D medical appliances, and so on.

In a specific implementation, the dynamic manufacturer selection model managing engine 812 is configured to determine potential manufacturer candidates by applying a patient record, a treatment plan, and manufacturer records to a dynamic manufacturer selection model. Depending upon implementation-specific or other considerations, one or more 3D medical appliance manufacturers whose manufacturer records match the treatment plan and/or the patient record may be selected as the potential manufacturer candidates.

In a specific implementation, the dynamic manufacturer selection model managing engine 812 is configured to provide information on the potential manufacturer candidates (e.g., the manufacturer records) to a patient system and/or a medical practitioner system, such that the patient or the medical practitioner can select one of the potential manufacturer candidates who is going to manufacture patient-specific 3D medical appliances. Further, in a specific implementation, upon selection of one of the potential manufacturer candidates by the patient or the medical practitioner, the dynamic manufacturer selection model managing engine 812 is configured to receive user selection inputs indicating one of the potential manufacturer candidates, and provides a patient record and a treatment plan to a 3D medical appliance manufacturer system of the selected manufacturer upon reception of the user selection inputs.

In a specific implementation, the dynamic manufacturer selection model managing engine 812 is configured to receive user feedback from a patient system and/or a medical practitioner system. Depending upon implementation-specific or other considerations, the user feedback may include practitioner applicability (e.g., how service conditions provided by practitioner matches patient's treatment conditions), quality of practitioner service (QoS) determined subjectively by the patient, manufacturer applicability (e.g., how appliance conditions provided by manufacturer matches the treatment plan), quality of manufacturer service (QoS) determined subjectively by the patient and/or the practitioner. Further, in a specific implementation, the dynamic manufacturer selection model managing engine 812 is configured to modify the dynamic manufacturer selection model based on the user feedback. In a specific implementation, the dynamic manufacturer selection model managing engine 812 modifies specific parameter values and/or weighting balance of parameters of the dynamic manufacturer selection model, in accordance with an applicable machine learning technique such as a decision tree learning, association rule learning, artificial neural networks, deep learning, etc.

The dynamic manufacturer selection model datastore 814 is intended to represent a datastore to store one or more dynamic manufacturer selection models generated by the dynamic manufacturer selection model managing engine 812. In a specific implementation, in storing one or more dynamic manufacturer selection models, the dynamic manufacturer selection model datastore 814 manages the stored dynamic manufacturer selection models in a same or similar manner as the dynamic practitioner matching recommendation model datastore 514 in FIG. 5 storing the dynamic medical practitioner matching recommendation models.

In an example of operation of the example system shown in FIG. 8, the manufacturer selection communicating engine 802 communicates with a 3D medical appliance manufacturer system to obtain manufacturer information, and with a patient system and/or a medical practitioner system to provide information on potential manufacturer candidates for selection of one of the potential manufacturer candidates. The treatment plan processing engine 804 generates a treatment plan and stores the generated treatment plan in the treatment plan datastore 806. The manufacturer record processing engine 808 generates a manufacturer record based on manufacturer information obtained through the manufacturer selection communicating engine 802, and stores the generated manufacturer record in the manufacturer record datastore 810. The dynamic manufacturer selection model managing engine 812 generates a dynamic manufacturer selection model and stores the generated manufacturer selection model in the dynamic manufacturer selection model datastore 814.

Further, in an example of operation of the example system shown in FIG. 8, the dynamic manufacturer selection model managing engine 812 determines potential manufacturer candidates using the dynamic manufacturer selection model. The dynamic manufacturer selection model managing engine 812 receives user selection inputs to select one of the potential manufacturer candidates, provides a treatment plan and a patient record to a manufacturer system of the selected manufacturer. The dynamic manufacturer selection model managing engine 812 receives user feedback from a patient system and/or a medical practitioner system, and modifies the dynamic manufacturer selection model based on the user feedback.

Figure 9:
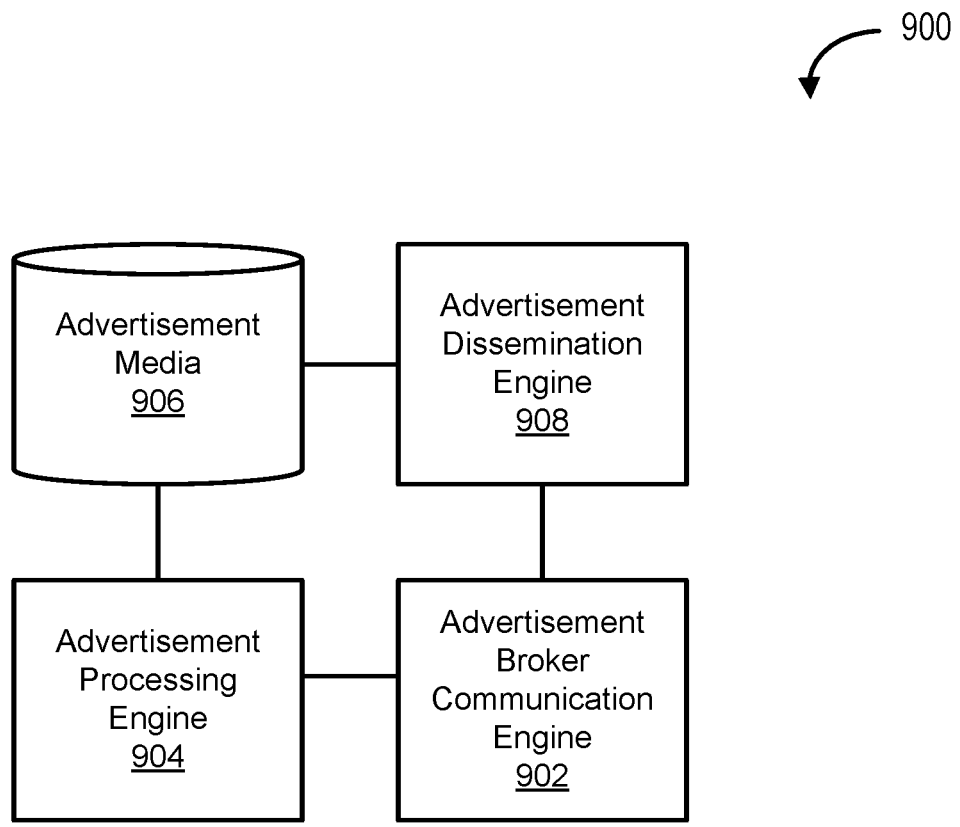
FIG. 9 is a block diagram of an example of an advertisement broker system included in a system for providing medical treatment that includes a 3D-printed medical appliance.

FIG. 9 is a block diagram 900 of an example of an advertisement broker system included in a system for providing medical treatment that includes a 3D-printed medical appliance. The example of the advertisement broker system shown in FIG. 9 includes an advertisement broker communication engine 902, an advertisement processing engine 904 coupled to the advertisement broker communication engine 902, advertisement media datastore 906 coupled to the advertisement processing engine 904, and an advertisement dissemination engine 908 coupled to the advertisement media datastore 906 and the advertisement broker communication engine 902. In a specific implementation, the advertisement broker system depicted in FIG. 9 corresponds to the advertisement broker system 112 in FIG. 1.

The advertisement broker communication engine 902 is intended to represent hardware configured to communicate with a medical practitioner system, a manufacturer system, and a patient system. In a specific implementation, in communicating with a medical practitioner system and/or a manufacturer system patient system, the advertisement broker communication engine 902 receives advertisement requests to propagate advertisement for a 3D-printed medical appliance, a 3D-printed accessory, and/or related services. Depending upon implementation-specific or other considerations, advertisement requests may involve payment transaction before or after performing advertisement services. In a specific implementation, in communicating with a medical practitioner system and/or a manufacturer system patient system, the advertisement broker communication engine 902 receives patient records to be used for advertisement. Depending upon implementation-specific or other considerations, patient records used for advertisement may include pre-treatment state (e.g., picture of patient's body part). In a specific implementation, in communicating with a patient system, the advertisement broker communication engine 902 is configured to send a request for advertisement use consent and receive advertisement use consent returned from a patient system. Depending upon implementation-specific or other considerations, the advertisement use consent may be obtained before or after a 3D-printed medical appliance based treatment is performed.

The advertisement processing engine 904 is intended to represent hardware configured to generate advertisement images based on patient records. In a specific implementation, an advertisement image may include pictures of patient's body part showing the pre-treatment state, the state after application of a 3D-printed medical appliance, or modified images of the patient's body part or 3D-printed medical appliance for advertisement purpose (e.g., changing color, concealing portion of images, etc.).

In a specific implementation, the advertisement processing engine 904 is configured to generate a dynamic advertisement selection model. Depending upon implementation-specific or other considerations, the dynamic advertisement selection model is configured to determine one or more advertisement images to be propagated and/or advertisement media based on attributes of the advertisement images and attributes of an advertisement request. In a specific implementation, the dynamic advertisement selection model may include a plurality of parameters for determining resulting advertisement images and/or advertisement media for a specific advertiser (e.g., a medical practitioner, a manufacturer, etc.), and parameter values of the parameters may be modified through applicable machine learning techniques. In a specific implementation, the parameters of the dynamic advertisement selection model may include a geographical location of distribution (e.g., country, state, county, city, etc.), time, exposure amount (e.g., view counts), target advertisement receiver attributes, and so on.

In a specific implementation, the advertisement processing engine 904 is configured to determine advertisements to be distributed by applying attributes of advertisement media and attributes of advertisement requests to a dynamic advertisement selection model. Depending upon implementation-specific or other considerations, one or more advertisement images that match advertisement requests may be selected as the advertisement images to be distributed.

In a specific implementation, the advertisement processing engine 904 is configured to obtain advertisement outcome. Depending upon implementation-specific or other considerations, the advertisement outcome may include statistical data regarding sales of 3D-printed medical appliance treatment services, sales of 3D-printed appliance medical appliances, sales of 3D-printed accessories, access counts to link associated with disseminated advertisement, and other applicable marketing criteria. Further, in a specific implementation, the advertisement processing engine 904 is configured to modify the dynamic advertisement selection model based on the advertisement outcome. In a specific implementation, the advertisement processing engine 904 modifies specific parameter values and/or weighting balance of parameters of the dynamic advertisement selection model, in accordance with an applicable machine learning technique such as a decision tree learning, association rule learning, artificial neural networks, deep learning, etc.

The advertisement media datastore 906 is intended to represent a datastore to store one or more advertisement images, audio files, or multimedia files generated by the advertisement processing engine 904. In a specific implementation, in storing advertisement media, the advertisement media datastore 906 manages the stored advertisement media using an advertisement media table including a plurality of entries each of which corresponds to advertisement media content. For example, an entry of the advertisement media table includes an identification of the advertisement image, an identification of a patient, parameter values associated with the advertisement media table, and stored location information of the advertisement image. In a specific implementation, in storing advertisement media, the advertisement media datastore 906 also stores a machine learning model applicable to one or more patient records stored therein.

The advertisement dissemination engine 908 is intended to represent hardware configured to provide advertisements that are determined to be distributed to an advertisement platform corresponding to the determined advertisement media. In a specific implementation, an advertisement platform may include a specific website, a specific web application, a specific TV program, a specific radio program, a specific radio program, social channels, and other applicable platforms.

In an example of operation of the example system shown in FIG. 9, the advertisement broker communication engine 902 communicates with a medical practitioner system and/or a manufacturer system to receive advertisement requests and patient records, and with a patient system for advertisement use consent. The advertisement processing engine 904 generates advertisement images based on patient records, and stores the generated advertisement images in the advertisement image datastore 906. The advertisement processing engine 904 generates a dynamic advertisement selection model, and determines advertisement images to be propagated and advertisement media, using the dynamic advertisement selection model. The advertisement dissemination engine 908 provides determined advertise images to an advertisement platform corresponding to the determined advertisement media. The advertisement processing engine 904 obtains advertisement outcome, and modifies the dynamic advertisement selection model based on the advertisement outcome.

Figure 10:
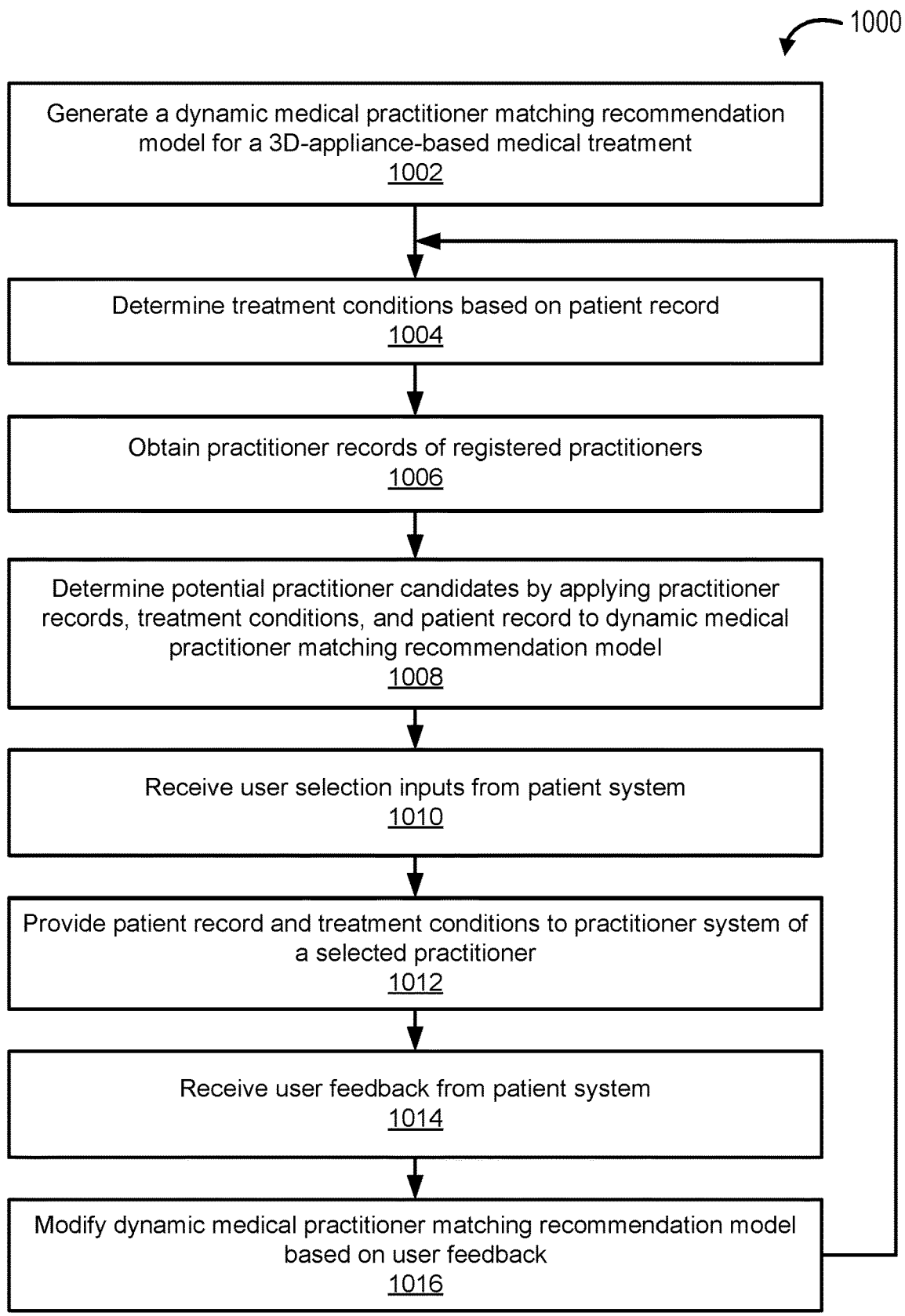
FIG. 10 is a flowchart of an example of a method for providing a practitioner matching recommendation service.

FIG. 10 is a flowchart 1000 of an example of a method for providing a practitioner matching recommendation service. This flowchart and the other flowcharts described in this paper illustrate modules (and potentially decision points) organized in a fashion that is conducive to understanding. It should be recognized, however, that the modules can be reorganized for parallel execution, reordered, modified (changed, removed, or augmented), where circumstances permit. The flowchart 1000 begins at module 1002 with generating a dynamic medical practitioner matching recommendation model for a 3D-appliance-based medical treatment. An applicable engine such as a dynamic practitioner matching recommendation model managing engine described in this paper generates a dynamic medical practitioner matching recommendation model. Depending upon implementation-specific or other considerations, the dynamic medical practitioner matching recommendation model may include a geographical location of a patient, patient's preferences, and a geographical location, schedules, practice field, price range, and rating of a practitioner, as parameters.

The flowchart 1000 continues to module 1004 with determining treatment conditions based on a patient record. An applicable engine such as a patient record processing engine described in this paper determines treatment conditions based on a patient record. In a specific implementation, the patient record may include attribute information (e.g., age, gender, race, residence, etc.) of a patient and information on a pre-treatment state (e.g., pre-treatment tooth arrangement) of a patient. For example, the information on the pre-treatment state may include self-captured 2D pictures of a patient body part (e.g., teeth), and may not include detailed 3D scanning data. In a specific implementation, the treatment conditions of a treatment (e.g., orthodontic treatment) may include a budget range, a term (e.g., time length) of treatment, a post-treatment state (e.g., post-treatment tooth arrangement), an acceptable pain level, and so on. Depending upon implementation-specific or other considerations, the treatment conditions may be determined also based on inputs by the patient through an applicable system such as a patient system described in this paper.

The flowchart 1000 continues to module 1006 with obtaining practitioner records of registered practitioners. An applicable engine such as a practitioner record processing engine described in this paper obtains practitioner records of registered practitioners. In a specific implementation, practitioner records of registered practitioners include a geographical location, schedules, practice field, price range, and rating of registered practitioners. Depending upon implementation-specific or other considerations, information included in practitioner records are obtained based on inputs by medical practitioners through an applicable system such as a medical practitioner system described in this paper.

The flowchart 1000 continues to module 1008 with determining potential practitioner candidates by applying practitioner records, treatment conditions, and the patient record to the dynamic medical practitioner matching recommendation model. An applicable engine such as a dynamic practitioner matching recommendation model managing engine described in this paper determines potential practitioner candidates. Depending upon implementation-specific or other considerations, one or more practitioners whose practitioner records match treatment conditions and/or the patient record may be selected as the potential practitioner candidates. In a specific implementation, information of the potential practitioner candidates are provided to the patient through a patient system such that the patient can review the information.

The flowchart 1000 continues to module 1010 with receiving user selection inputs from patient system. An applicable engine such as a matching data communicating engine described in this paper receives the user selection inputs. Depending upon implementation-specific or other considerations, the user selection inputs may include information on a medical practitioner selected by the patient.

The flowchart 1000 continues to module 1012 with providing the patient record and treatment conditions to a practitioner system of a selected practitioner. An applicable engine such as a patient record processing engine described in this paper retrieves the patient record and the treatment conditions of the patient and causes the patient record and the treatment conditions of the patient to be provided to a medical practitioner system of the selected practitioner, such that the selected practitioner can review the patient record and the treatment conditions and schedule consultation and/or treatment.

The flowchart 1000 continues to module 1014 with receiving user feedback from a patient system. An applicable engine such as a matching data communicating engine described in this paper receives the user feedback from a patient system. Depending upon implementation-specific or other considerations, the user feedback may include applicability (e.g., how service conditions provided by practitioner matches patient's treatment conditions) and quality of service (QoS) determined subjectively by the patient.

The flowchart 1000 ends at module 1016 with modifying the dynamic medical practitioner matching recommendation model based on the user feedback. An applicable engine such as a dynamic practitioner matching recommendation model managing engine described in this paper modifies the dynamic medical practitioner matching recommendation model based on the user feedback. In a specific implementation, specific parameter values and/or weighting balance of parameters of the dynamic medical practitioner matching recommendation model are modified, in accordance with an applicable machine learning technique such as a decision tree learning, association rule learning, artificial neural networks, deep learning, etc. After module 1016, the flowchart 1000 returns to module 1004 for new practitioner matching.

Figure 11:
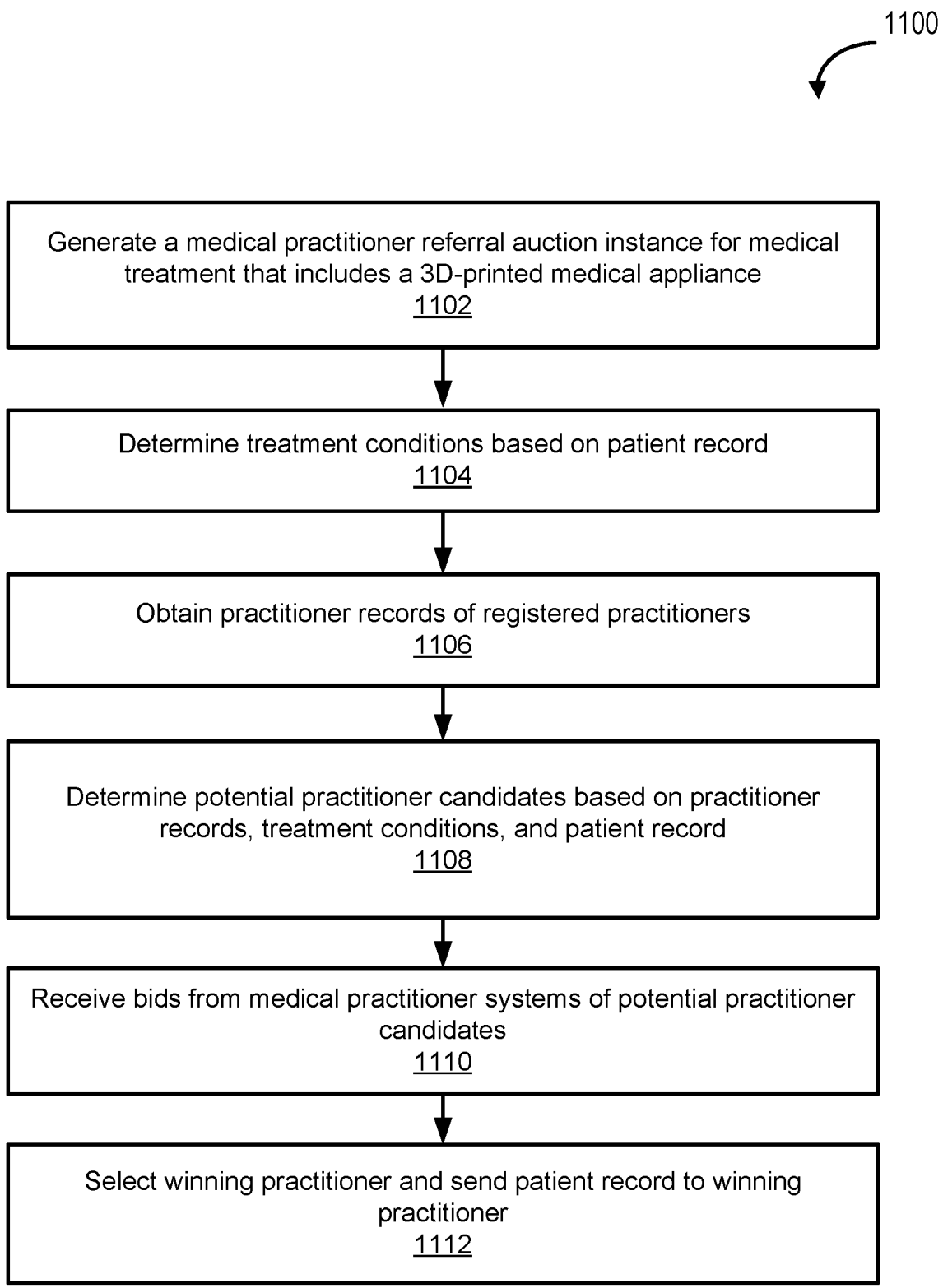
FIG. 11 is a flowchart of an example of a method for providing a practitioner referral auction service.

FIG. 11 is a flowchart 1100 of an example of a method for providing a practitioner referral auction service. The flowchart 1100 begins at module 1102 with generating a medical practitioner referral auction instance for medical treatment that includes a 3D-printed medical appliance. An applicable engine such as a practitioner referral auction engine described in this paper generates a medical practitioner referral auction instance.

The flowchart 1100 continues to module 1104 with determining treatment conditions based on a patient record. An applicable engine such as a patient record processing engine described in this paper determines treatment conditions based on a patient record. In a specific implementation, the module 1104 can be carried out in a similar manner as module 1004 in FIG. 10.

The flowchart 1100 continues to module 1106 with obtaining practitioner records of registered practitioners. An applicable engine such as a practitioner record processing engine described in this paper obtains practitioner records of registered practitioners. In a specific implementation, the module 1106 can be carried out in a similar manner as module 1006 in FIG. 10.

The flowchart 1100 continues to module 1108 with determining potential practitioner candidates based on practitioner records, treatment conditions, and the patient record. An applicable engine such as a practitioner referral auction engine described in this paper determines potential practitioner candidates. Depending upon implementation-specific or other considerations, one or more practitioners whose practitioner records match treatment conditions and/or the patient record may be selected as the potential practitioner candidates. In a specific implementation, information of treatment conditions are provided to medical practitioner systems of the potential practitioner candidates such that they can review the information.

The flowchart 1100 continues to module 1110 with receiving bids from medical practitioner systems of potential practitioner candidates. An applicable engine such as an auction data communicating engine described in this paper receives bids from medical practitioner systems of potential practitioner candidates. In a specific implementation, a bid includes a specific value indicating a pricing for a treatment and a timestamp. Practitioners could also create pre-sets for these values for a certain case type to enable an auto-bid feature.

The flowchart 1100 ends at module 1112 with selecting winning practitioner candidates and sending a complete patient record and treatment conditions information to the winning practitioner. An applicable engine such as a practitioner referral auction engine described in this paper selects a winning practitioner and sends the complete patient record and treatment conditions to the winning practitioner. In a specific implementation, bid amount, timestamp, other applicable criteria may be employed to select the winning practitioner.

Figure 12:
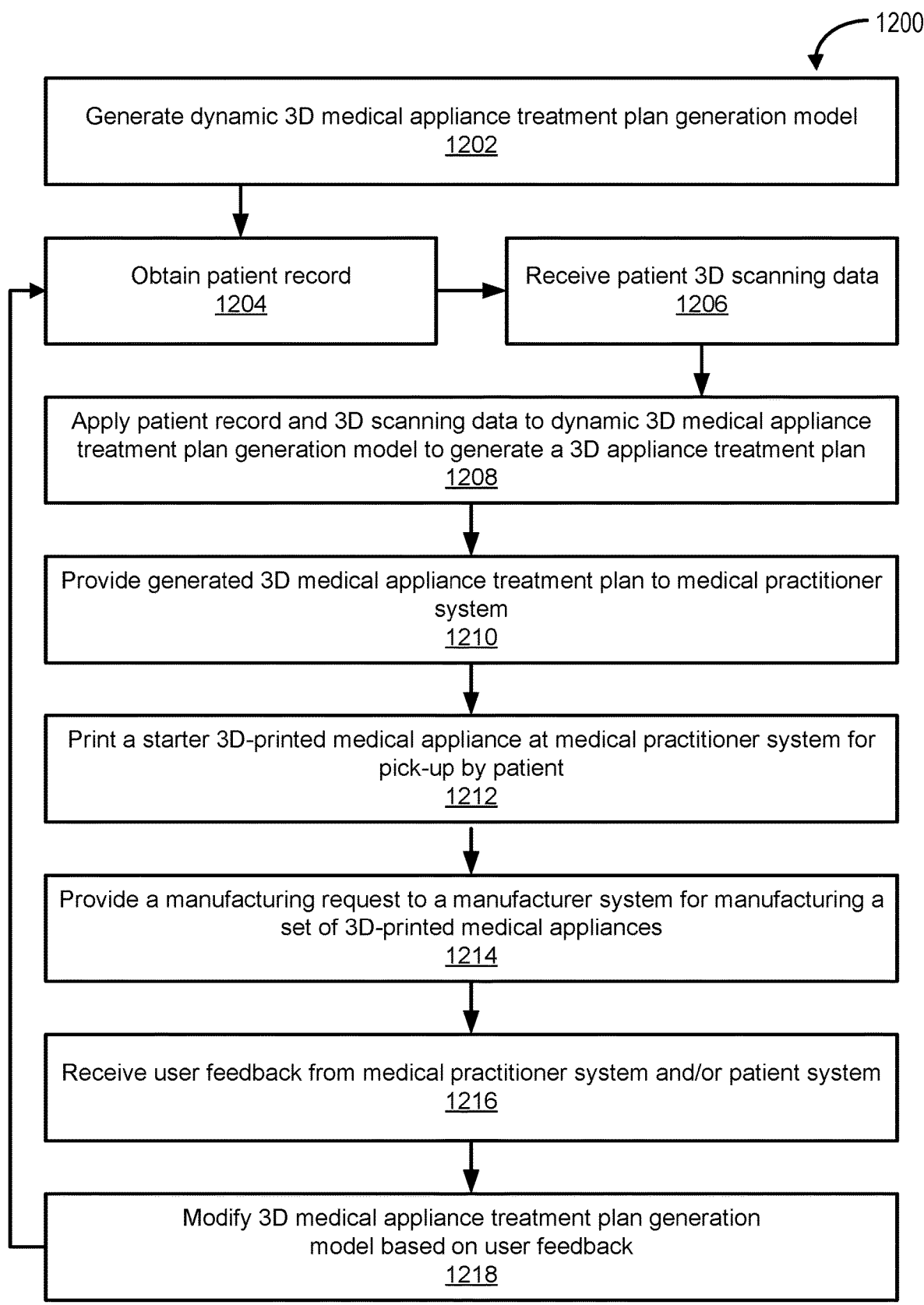
FIG. 12 is a flowchart of an example of a method for generating a 3D medical appliance treatment plan and providing a set of 3D medical appliances based on the 3D medical appliance treatment plan.

FIG. 12 is a flowchart 1200 of an example of a method for generating a 3D medical appliance treatment plan and providing a set of 3D medical appliances based on the 3D medical appliance treatment plan. The flowchart 1200 begins at module 1202 with generating a dynamic 3D medical appliance treatment plan generation model. An applicable engine such as a dynamic treatment plan generation model managing engine described in this paper generates the dynamic 3D medical appliance treatment plan generation model. Depending upon implementation-specific or other considerations, the dynamic 3D medical appliance treatment plan generation model may include a pre-treatment state of a patient, an expected post-treatment state of the patient, a treatment term (e.g., length of time and phases), expected pain levels, a budget range, and so on as parameters.

The flowchart 1200 continues to module 1204 with obtaining a patient record. An applicable engine such as a patient record processing engine described in this paper obtains a patient record of a patient. In a specific implementation, the patient record may include attribute information (e.g., age, gender, race, residence, etc.) of a patient and information on a pre-treatment state (e.g., pre-treatment tooth arrangement) of a patient. For example, the information on the pre-treatment state may include self-captured 2D pictures of a patient body part (e.g., teeth), and may not include detailed 3D scanning data.

The flowchart 1200 continues to module 1206 with receiving 3D scanning data of a patient. An applicable engine such as a treatment plan communicating engine described in this paper receives 3D scanning data of a patient from an applicable sources, such as a medical practitioner system and/or a patient system. In a specific implementation, when a medical practitioner system includes a 3D scanning device to obtain 3D scanning data of the patient, the 3D scanning data are transmitted from the medical practitioner system. In a specific implementation, when a medical practitioner obtains an impress of a patient's body part, the impress may be delivered, and the 3D scanning data may be obtained by scanning the impress.

The flowchart 1200 continues to module 1208 with generating a 3D appliance treatment plan by applying the patient record and the 3D scanning data to the dynamic 3D medical appliance treatment plan generation model. An applicable engine such as a dynamic treatment plan generation model managing engine described in this paper generates the 3D appliance treatment plan. In a specific implementation, a 3D appliance treatment plan may include an expected post-treatment state of the patient, a treatment term (e.g., length of time and phases), expected pain levels, an estimated price, types and designs of 3D medical appliances to be used for each of different phases of the treatment, and manner and duration of attaching 3D medical appliances, and so on. For example, types and designs of 3D medical appliances may include materials, color, and -patient-specific shape of the 3D medical appliances. For example, the manner and duration of attaching 3D medical appliances may include acceptable patient's movement or activity during attachment of the 3D medical appliances, and a time range in a day, week, or month during which the 3D medical appliances should be attached.

The flowchart 1200 continues to module 1210 with providing the generated 3D medical appliance treatment plan to a medical practitioner system. An applicable engine such as a treatment plan communicating engine described in this paper provides the generated 3D medical appliance treatment plan to a medical practitioner system, such that a medical practitioner can review the generated 3D medical appliance treatment plan for approval. In a specific implementation, the generated 3D medical appliance treatment plan is also provided to the patient by the medical practitioner or directly provided to a patient system, for the patient's consent. In a specific implementation, the medical practitioner's approval of the 3D medical appliance treatment plan and/or the patient's consent of the 3D medical appliance treatment plan are returned for further processing.

The flowchart 1200 continues to module 1212 with printing a starter 3D-printed medical appliance at a medical practitioner system for pick-up by patient. An applicable device such as a local 3D printer of a medical practitioner system can manufacture the instant starter 3D-printed medical appliance. Advantageously, the starter 3D-printed medical appliance can be printed in advance of a meeting with the patient (if the patient sends images or if the images are available via, for example, dental records at a dentist office). Alternatively, the starter 3D-printed medical appliance can be printed during consultation or after a short wait, allowing the patient to leave with the starter 3D-printed medical appliance. Advantageously, such appliances can be properly characterized as, in the case of aligners, "same-day aligners," or "aligners available in less than one hour." In dental, medical, and beauty product contexts, the aligners can be made available while sitting for some other procedure, and can properly be characterized as "no-wait aligners" because the aligners can be provided before some other procedure (e.g., haircut, pedicure, etc.) is finished. In a specific implementation, the patient's consent may be made before printing the starter 3D-printed medical appliance.

The flowchart 1200 continues to module 1214 with providing a manufacturing request to a manufacturer system for manufacturing a set of 3D medical appliances. An applicable engine such as a treatment plan communicating engine described in this paper provides the manufacturing request with the approved 3D appliance treatment plan to a manufacturer system. In a specific implementation, a manufacturer system manufactures a set of 3D-printed medical appliances specifically designed for the patient based on the approved 3D appliance treatment plan. In a specific implementation, manufactured 3D medical appliances may be inspected by a medical practitioner or other professionals (e.g., technician) and may be re-manufactured depending upon whether the manufactured 3D medical appliances meet standards of the manufacturing request. In a specific implementation, manufactured 3D medical appliances are delivered to the patient, such that the patient wears the 3D medical appliances for the treatment.

The flowchart 1200 continues to module 1216 with receiving user feedback from a medical practitioner system and/or a patient system. An applicable engine such as a treatment plan communicating engine described in this paper receives the user feedback. Depending upon implementation-specific or other considerations, the user feedback may include practitioner applicability (e.g., how service conditions provided by practitioner matches patient's treatment conditions), quality of practitioner service (QoS) determined subjectively by the patient, manufacturer applicability (e.g., how appliance conditions provided by manufacturer matches the treatment plan), quality of manufacturer service (QoS) determined subjectively by the patient and/or the practitioner.

The flowchart 1200 ends at module 1218 with modifying the dynamic 3D medical appliance treatment plan generation model based on the user feedback. An applicable engine such as a dynamic treatment plan generation model managing engine described in this paper modifies the dynamic 3D medical appliance treatment plan generation model. In a specific implementation, specific parameter values and/or weighting balance of parameters of the dynamic 3D medical appliance treatment plan generation model are modified, in accordance with an applicable machine learning technique such as a decision tree learning, association rule learning, artificial neural networks, deep learning, etc. After module 1218, the flowchart 1200 returns to module 1204 for a new treatment plan.

Figure 13:
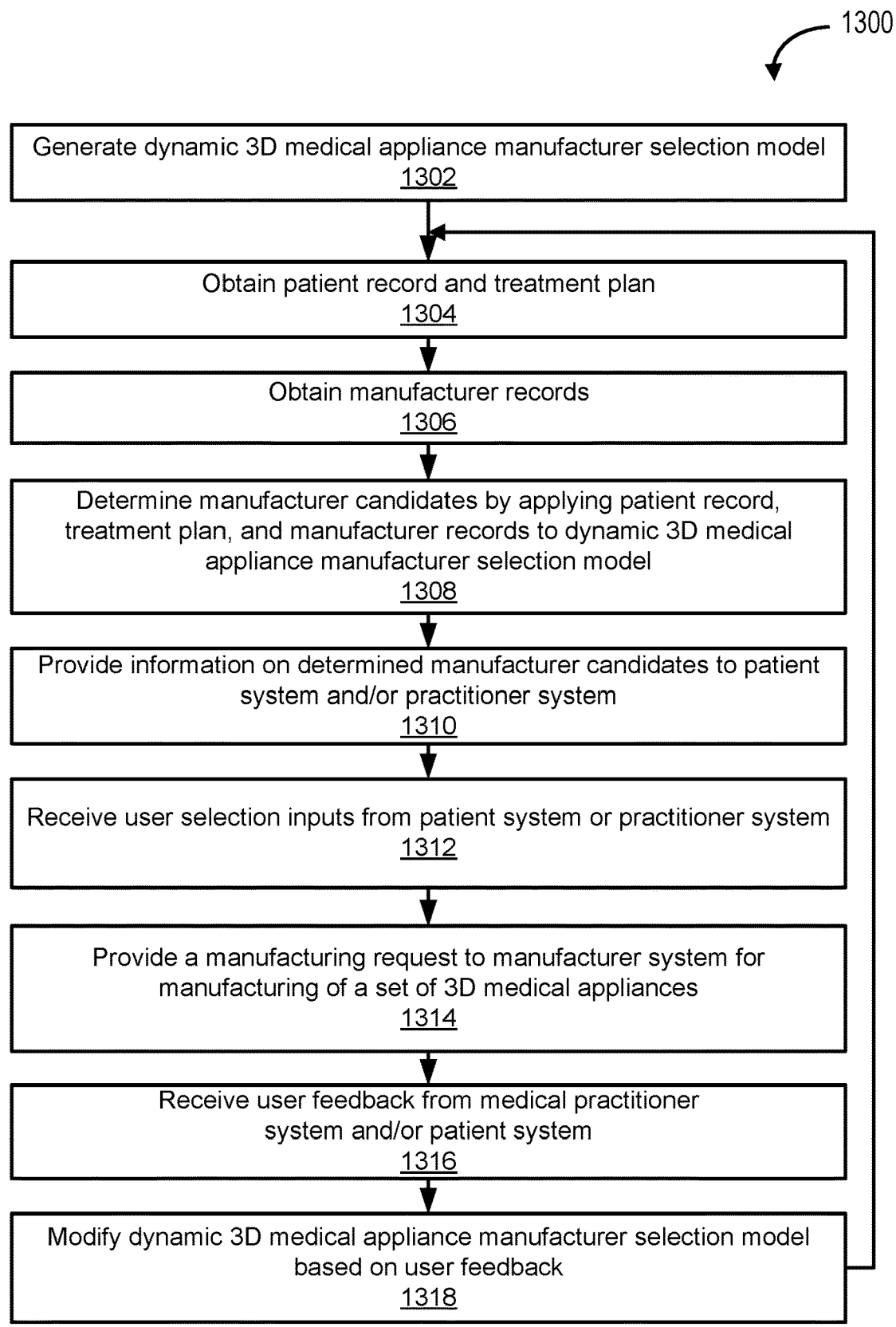
FIG. 13 is a flowchart of an example of a method for providing a 3D medical appliance manufacturer selection service.

FIG. 13 is a flowchart 1300 of an example of a method for providing a 3D medical appliance manufacturer selection service. The flowchart 1300 begins at module 1302 with generating a dynamic 3D medical appliance manufacturer selection model. An applicable engine such as a dynamic manufacturer selection model managing engine described in this paper generates the dynamic 3D medical appliance manufacturer selection model. Depending upon implementation-specific or other considerations, the dynamic 3D medical appliance manufacturer selection model may include a geographical region of the manufacturer, manufactured appliance type and design, price range, on-time delivery rating, practitioner rating, patient rating, and so on.

The flowchart 1300 continues to module 1304 with obtaining a patient record and a treatment plan. An applicable engine such as a patient record processing engine described in this paper obtains a patient record and a treatment plan of a patient. In a specific implementation, a treatment plan of a patient can be generated through an applicable process such as the one described in FIG. 12.

The flowchart 1300 continues to module 1306 with obtaining manufacturer records. An applicable engine such as a manufacturer record processing engine described in this paper obtains manufacturer records of registered manufacturers. In a specific implementation, manufacturer records of registered manufacturers include a geographical location, expected delivery time, manufactured appliance type and design, price range, on-time delivery rating, practitioner rating, patient rating, and so on. Depending upon implementation-specific or other considerations, information included in manufacturer records are obtained at least partially based on inputs by manufacturer through an applicable system such as a manufacturer system described in this paper.

The flowchart 1300 continues to module 1308 with determining manufacturer candidates by applying the patient record, the treatment plan, and the manufacturer records to the dynamic 3D medical appliance manufacturer selection model. An applicable engine such as a dynamic manufacturer selection model managing engine described in this paper determines manufacturer candidates. Depending upon implementation-specific or other considerations, one or more 3D-printed medical appliance manufacturers whose manufacturer records match the patient record and/or the treatment plan may be selected as the manufacturer candidates. In a specific implementation, information of the treatment plan, in particular type and design of 3D-printed medical appliances for the patient is provided to manufacturers systems of the manufacturer candidates such that they can review the information.

The flowchart 1300 continues to module 1310 with providing information on manufacturer candidates to a patient system or a practitioner system. An applicable engine such as a manufacturer selection communicating engine described in this paper provides the information on manufacturer candidates to a patient system or a practitioner system, such that the patient system or the practitioner system can present the information for selection of a 3D-printed medical appliance manufacturer.

The flowchart 1300 continues to module 1312 with receiving user selection inputs from the patient system or the practitioner system. An applicable engine such as a manufacturer selection communicating engine described in this paper receives the user selection inputs. Depending upon implementation-specific or other considerations, the user selection inputs may include information on a 3D-printed medical appliance manufacturer selected by the patient or the medical practitioner.

The flowchart 1300 continues to module 1314 with providing a manufacturing request to a selected manufacturer system for manufacturing a set of 3D medical appliances. An applicable engine such as a manufacturer selection communicating engine described in this paper provides the manufacturing request with the approved 3D appliance treatment plan to the selected manufacturer system. In a specific implementation, the module 1314 can be carried out in a similar manner as module 1214 in FIG. 12.

The flowchart 1300 continues to module 1316 with receiving user feedback from a medical practitioner system and/or a patient system. An applicable engine such as a manufacturer selection communicating engine described in this paper receives the user feedback. In a specific implementation, the module 1316 can be carried out in a similar manner as module 1216 in FIG. 12.

The flowchart 1300 ends at module 1318 with modifying the dynamic 3D medical appliance manufacturer selection model based on the user feedback. An applicable engine such as a dynamic manufacturer selection model managing engine described in this paper modifies the dynamic manufacturer selection model. In a specific implementation, specific parameter values and/or weighting balance of parameters of the dynamic manufacturer selection model are modified, in accordance with an applicable machine learning technique such as a decision tree learning, association rule learning, artificial neural networks, deep learning, etc. After module 1318, the flowchart 1300 returns to module 1304 for new manufacturer selection.

Figure 14:
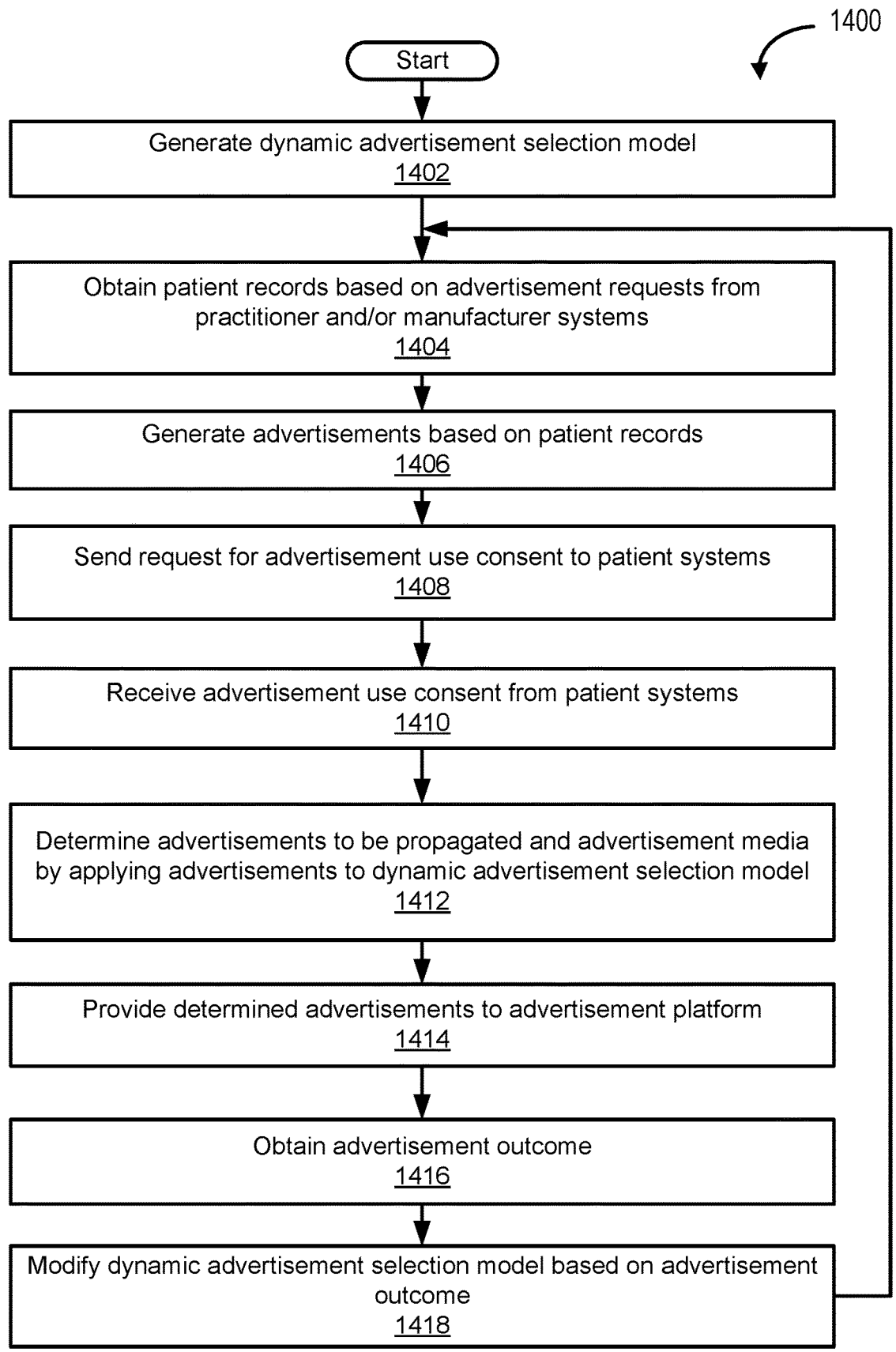
FIG. 14 is a flowchart of an example of a method for providing a 3D-printed advertisement service.

FIG. 14 is a flowchart 1400 of an example of a method for providing a 3D-printed advertisement service. The flowchart 1400 begins at module 1402 with generating a dynamic advertisement selection model. An applicable engine such as an advertisement processing engine described in this paper generates the dynamic advertisement selection model. Depending upon implementation-specific or other considerations, the dynamic advertisement selection model may include a target geographical region of advertisement receivers, target advertisement receiver attributes (e.g., age, gender, race, income level, etc.), advertisement attributes (e.g., types and nature of service, products, etc.), duration, budget range, and so on.

The flowchart 1400 continues to module 1404 with obtaining patient records based on advertisement requests from practitioner and/or manufacturer systems. An applicable engine such as an advertisement broker communication engine described in this paper receives advertisement requests from practitioner and/or manufacturer systems and obtains patient records. Depending upon implementation-specific or other considerations, patient records used for advertisement may include pre-treatment state (e.g., picture of patient's body part) and pre-treatment state (e.g., picture of patient's body part).

The flowchart 1400 continues to module 1406 with generating advertisements based on the patient records. An applicable engine such as an advertisement processing engine described in this paper generates advertisements based on the patient records. In a specific implementation, an advertisement may include pictures of patient's body part showing the pre-treatment state and the post-treatment state, a mock-up of the patient's body with a medical appliance attached, or modified images of the patient's body part or appliance for advertisement purpose (e.g., changing color, concealing portion of images, etc.).

The flowchart 1400 continues to module 1408 with sending a request for advertisement use consent to patient systems. An applicable engine such as an advertisement broker communication engine described in this paper sends the request for advertisement use consent to patient systems.

The flowchart 1400 continues to module 1410 with receiving advertisement use consent from patient systems. An applicable engine such as an advertisement broker communication engine described in this paper receives the advertisement use consent from the patient systems.

The flowchart 1400 continues to module 1412 with determining advertisements to be propagated and advertisement media on which advertisement is propagated by applying advertisements and advertisement requests to dynamic advertisement selection model. An applicable engine such as an advertisement processing engine described in this paper determining the advertisements to be propagated and the advertisement media. In a specific implementation, a target geographical region of advertisement receivers, target advertisement receiver attributes (e.g., age, gender, race, income level, etc.), advertisement attributes (e.g., types and nature of service, products, etc.), duration, budget range, and so on are extracted from an advertisement request and advertisement image having the similar attributes (e.g., age, gender, etc.) as the target advertisement receivers and/or advertisement media (e.g., specific websites, web browser, etc.) associated with the target advertisement receivers are determined.

The flowchart 1400 continues to module 1414 with providing determined advertisements to an advertisement platform corresponding to the determined advertisement media. An applicable engine such as an advertisement dissemination engine described in this paper provides determined advertise images to the advertisement platform. In a specific implementation, an advertisement platform may include a specific website, a specific web application, a specific TV program, a specific radio program, a specific radio program, social channels, and other applicable platforms.

The flowchart 1400 continues to module 1416 with obtaining advertisement outcome. An applicable engine such as an advertisement broker communication engine described in this paper obtains advertisement outcome. In a specific implementation, advertisement outcome may include statistic data indicating sales of 3D-printed medical appliance treatment service, sales of 3D-printed appliance medical appliances, access counts to link associated with disseminated advertisement, and other applicable marketing criteria.

The flowchart 1400 ends at module 1418 with modifying the dynamic advertisement selection model based on the advertisement outcome. An applicable engine such as an advertisement broker communication engine described in this paper modifies the dynamic advertisement selection model. In a specific implementation, specific parameter values and/or weighting balance of parameters of the dynamic advertisement selection model are modified, in accordance with an applicable machine learning technique such as a decision tree learning, association rule learning, artificial neural networks, deep learning, etc. After module 1418, the flowchart 1400 returns to module 1404 for new advertisement selection.

Figure 15:
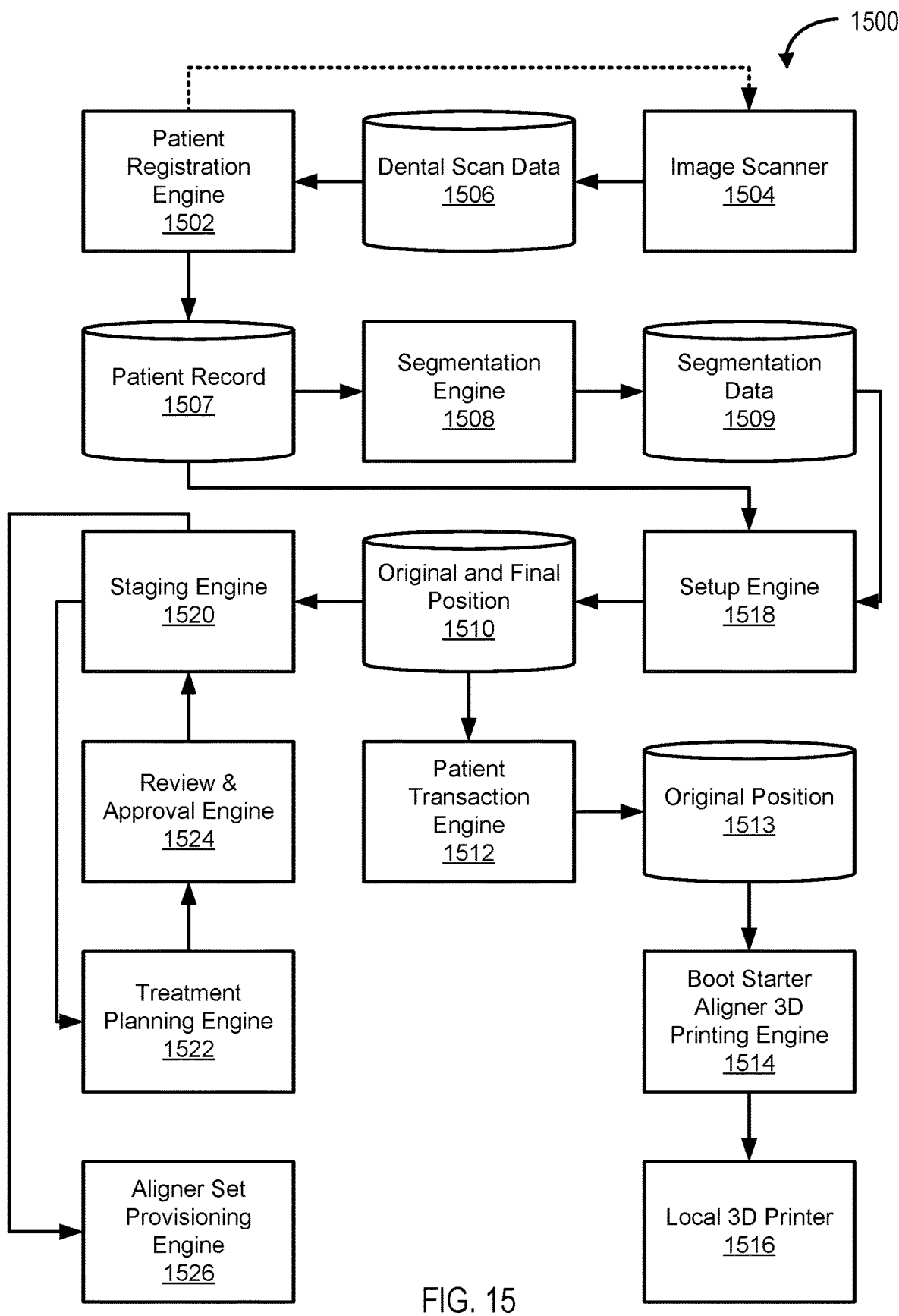
FIG. 15 is a block diagram of an example of elements in a system for providing medical treatment that includes a 3D-printed medical appliance.

FIG. 15 is a block diagram 1500 of an example of elements in a system for providing medical treatment that includes a 3D-printed medical appliance. For illustrative purposes, the system shown in FIG. 15 is directed for patient-specific 3D-printed dental appliances, such as an orthodontic aligner to be fit in a mouth of a patient. The system depicted in FIG. 15 includes a patient registration engine 1502, an image scanner 1504, dental scan data datastore 1506, a patient record datastore 1507, a segmentation engine 1508, final position datastore 1510, a patient transaction engine 1512, a boot starter aligner 3D printing engine 1514, a local 3D printer 1516, a setup engine 1518, a staging engine 1520, a treatment planning engine 1522, a review & approval engine 1524, and an aligner set provisioning engine 1526.

The patient registration engine 1502 is intended to represent hardware configured to register a patient who is going to receive dental treatment that includes a 3D-printed dental appliance. In a specific implementation, upon registration of the patient, a patient record, which include patient attributes, is generated and stored in the patient record datastore 1507. Patient registration may be partially complete if the treatment is initiated at a dental office because the dentist may already have records of the potential patient, perhaps even including adequate dental images.

The image scanner 1504 is intended to represent hardware configured to scan a patient's teeth to generate dental scan data. In a specific implementation, the image scanner 1504 includes a 3D scanner, coupled to a patient system and/or a medical practitioner system described in this paper, and the dental scan data include 3D scanning data. In a specific implementation, the image scanner 1504 includes a 2D camera, coupled to a patient system and/or a medical practitioner system described in this paper, and the dental scan data include 2D images.

The dental scan data datastore 1506 is intended to represent a datastore to store the generated dental scan data. In a specific implementation, the patient registration engine 1502 includes some or all of the images of the dental scan data datastore 1506 in an applicable patient record in the patient record datastore 1507. The dotted arrow from the patient registration engine 1502 to the image scanner 1504 is intended to represent that the image scanner 1504 may or may not have already created suitable images prior to patient registration. For example, a potential patient could have taken the images with a smart phone.

The segmentation engine 1508 is intended to represent hardware configured to perform segmentation of dental images of the patient. In a specific implementation, the segmentation includes identification and objectification of teeth and gums, mouth, lips, and potentially other parts, such as the tongue, and determination of location and coordinates of the identified objects.

The segmentation data datastore 1509 includes segmentation data. Because the segmentation data includes a coordinate system, the setup engine 1518 can use a function to transform the objects (teeth) into a subjectively ideal form, which is referred to as the final position.

The original and final position datastore 1510 is intended to represent a datastore to store the original and final position and orientation of a patient's teeth. It may be noted, final position can depend upon aesthetics that vary between different orthodontists (and patients) and the determination of final position is not traditionally considered part of the segmentation step; this paper assumes an appropriately configured AI (not shown) takes the segmentation data and manipulates it to reach a desired final position. Alternatively or in addition, the setup engine 1518 could generate additional intermediate positions, but that is assumed to be handled by the staging engine 1520 in this example.

The patient transaction engine 1512 is intended to represent hardware configured to perform transaction for 3D-printed medical appliance based dental treatment. In a specific implementation, the transaction includes contract document transaction between a patient and a dental practitioner, and payment for the 3D-printed medical appliance based dental treatment. It is likely to be desirable to be able to show original and final positions to a potential patient, which is why the setup engine 1518 does at least enough work to provide a final position (or at least a final position mock-up) in the original and final position datastore 1510 for use by the patient transaction engine 1512.

The original position datastore 1513 is likely to be a part of the original and final position datastore 1510, but is illustrated separately to clearly show the boot starter aligner 3D printing engine 1514 needs only the original position coordinates, including other parameters of the mouth to ensure the aligner fits.

The boot starter aligner 3D printing engine 1514 is intended to represent hardware configured to generate 3D print data for a boot aligner based on the position of objects that represent teeth. In a specific implementation, the 3D print data includes a plurality of layers of 2D image data suited for 3D printing.

The local 3D printer 1516 is intended to represent hardware configured to produce a starter 3D aligner based on the 3D data generated by the boot starter aligner 3D printing engine 1514. In a specific implementation, the starter 3D aligner is intended for trial purpose and not for treatment purpose. For example, the starter 3D aligner does not have a patient-specific tooth profile, and generically formed to fit patient's gum curve.

The setup engine 1518 is intended to represent hardware configured to set up a teeth straightening treatment, upon transaction being completed by the patient transaction engine 1512. In setting up a teeth straightening treatment, the setup engine 1518 retrieves a patient record including the segmentation data and passes the original and final position data on to the staging engine 1520.

The staging engine 1520 is intended to represent hardware configured to determine parameters of a teeth straightening treatment using a set of aligners. In a specific implementation, the treatment parameters may include a budget range, a term (e.g., time length) of dental treatment, a post-treatment state (e.g., post-treatment tooth arrangement), an acceptable pain level, and so on.

The treatment planning engine 1522 is intended to represent hardware configured to generate a treatment plan based on the patient record and the treatment conditions. In a specific implementation, a treatment plan may include an expected post-treatment tooth arrangement of the patient, a treatment term (e.g., length of time and phases), expected pain levels, an estimated price, types and designs of 3D-printed medical appliances to be used for each of different phases of the treatment, and manner and duration of attaching 3D-printed medical appliances, and so on.

The review & approval engine 1524 is intended to represent hardware configured to present a treatment plan generated by the treatment planning engine 1522 to the patient, the dental practitioner, and/or an expert in the field of staging, and to receive approval of the treatment plan therefrom. In a specific implementation, control can be passed between the staging engine 1520, the treatment planning engine 1522, and the review & approval engine 1524 multiple times before passing control to the aligner set provisioning engine 1528.

The aligner set provisioning engine 1526 is intended to represent hardware configured to produce aligners for the patient, which are delivered to the patient. In a specific implementation, a set of aligners is 3D-printed at the same location as the boot aligner. In an alternative, the set of aligners is manufactured in a known or convenient manner because, unlike with the boot aligner, time is not necessarily of the essence.

Figure 16:
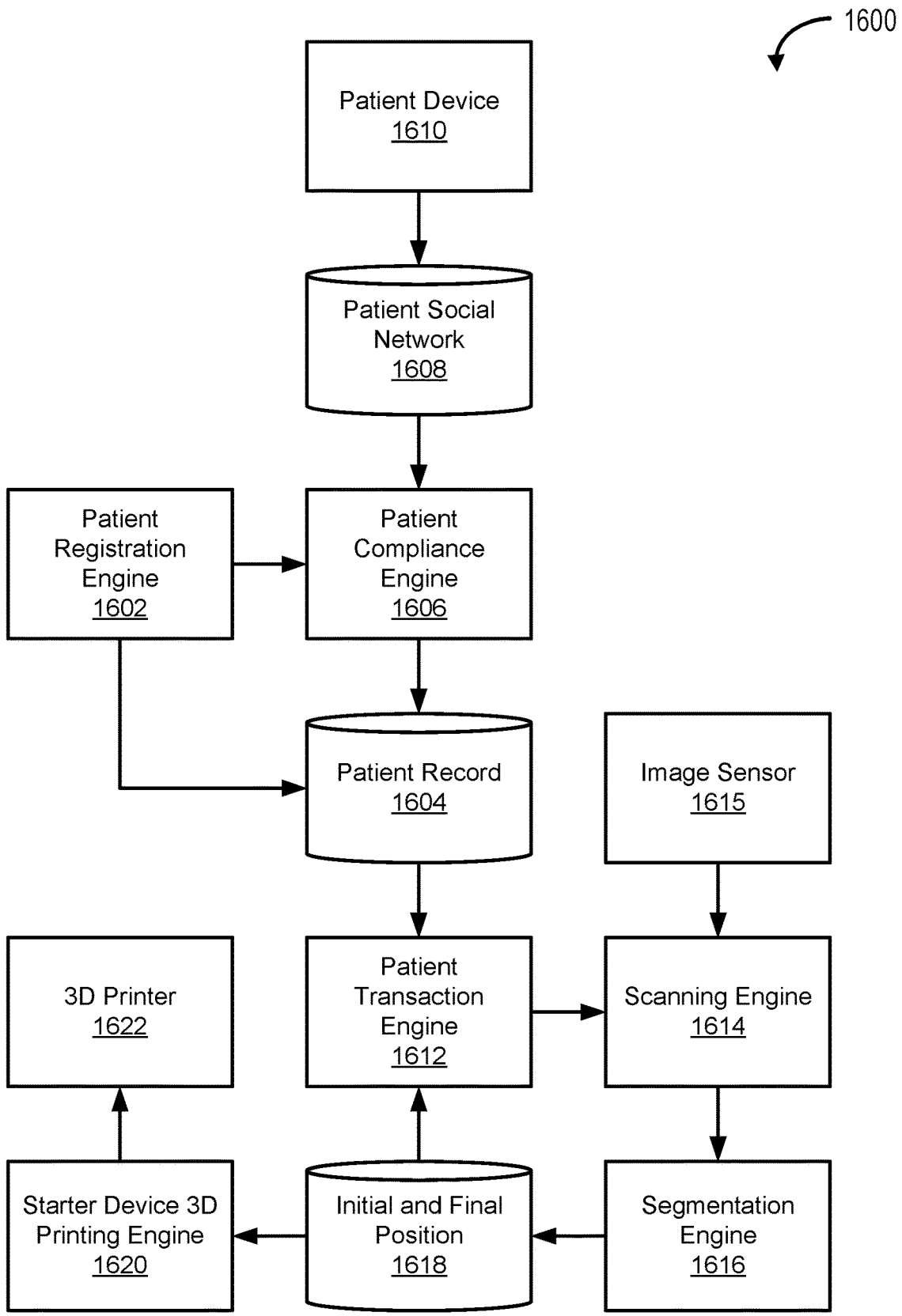
FIG. 16 is a block diagram of an example of a go-to-market system for 3D-printed appliances.

FIG. 16 is a block diagram 1600 of an example of a go-to-market system for 3D-printed appliances. The diagram 1600 includes a patient registration engine 1602, a patient record datastore 1604 coupled to the patient registration engine 1602, a patient compliance engine 1606 (aka API engine) coupled to the patient registration engine 1602 and the patient record datastore 1604, a patient social network datastore 1608 coupled to the patient compliance engine 1606, at least one patient device 1610 coupled to the patient social network datastore 1608, a patient transaction engine 1612 coupled to the patient record datastore 1604, a scanning engine 1614 coupled to the patient transaction engine 1612, an image sensor 1615 coupled to the scanning engine 1614, a segmentation engine 1616 coupled to the scanning engine 1614, an initial and final position datastore 1618 coupled to the patient transaction engine 1612 and the segmentation engine 1616, a starter device 3D printing engine 1620 coupled to the initial and final position datastore 1618, and a 3D printer 1622 coupled to the starter device 3D printing engine 1620. In a specific implementation, components described previously in this paper are configured to work with (or implemented in conjunction with) go-to-market components such as the patient compliance engine 1606 and the patient social network datastore 1608.

The patient registration engine 1602 is intended to represent hardware configured to register a patient who is going to receive a 3D-printed medical appliance based treatment. In a specific implementation, the patient registration engine 1602 depicted in FIG. 16 corresponds to the patient registration engine 304 in FIG. 3.

The patient record datastore 1604 is intended to represent a datastore of one or more patient records. In the example of FIG. 16, the patient record datastore 1604 includes information about patients in a customer loop that is updated as customers opt in, take action on social media, and take advantage of services. In a specific implementation, the patient record datastore 1604 depicted in FIG. 16 corresponds to the patient record datastore 506 in FIG. 5.

The patient compliance engine 1606 is intended to represent hardware configured to seek evidence of compliance with targets that have an impact on aspects of provided services. The patient compliance engine 1606 may also weed out bad, inappropriate, or otherwise non-compliant posts. In a specific implementation, the patient compliance engine includes multiple APIs that are suitable for interfacing with social network and other sources, such as Facebook, Instagram, Google, or the like. Patients can be informed about targets in person, such as in a dental office, at a kiosk, or the like, via physical media, such as flyers, letters, or magazine articles, or via electronic media, such as ads, blogs, or messaging. Targets can include, for example, blogs, vlogs, shout-outs, or the like, which are analyzed for quantity and, in some embodiments, quality, and may include prepared statements, images, and/or formats. For example, the potential patient may be requested to post am image of their face, a "favicon," and a unique customer barcode, optical code, or the like to facilitate identification of the potential patient who gets credit for the activity.

The perks of meeting targets can include discounts for services, subscription models, or the like, or to unlock special features, such as unique, rare, or otherwise desirable cosmetic items. In a specific implementation, the targets are set in accordance with break-even models and sliding scales designed to ensure activities by a potential patient are likely to increase profits for the service providers and/or other involved parties. In a specific implementation, artificial agents scour social media to track frequency of posting by potential patients, then compute an appropriate discount for such types of activities. Potential patients may also be identified using facial recognition, potentially including identification of correctable features, such as crooked teeth. The patient compliance engine 1606 stores perks, credits, or the like earned by potential patients in the patent record datastore 1604 in association with the potential patient who earned the perks, credits, or the like.

The patient social network datastore 1608 is intended to represent a datastore of content from social media networks. The patient social network datastore 1608 can be characterized as all social media content that is used by the patient compliance engine 1606, which may include long-term storage of the content or a buffer that lasts only as long as the content is being analyzed; the precise location of the data is not as important as its utility to the patient compliance engine 1606. In a specific implementation, an iframe on a homepage is fed by the patient compliance engine 1606, which finds potential patient posts that are fed live into the iframe. The potential patient receives credit for likes and getting friends to post likes, which can be used to get items or services from service providers or associated parties or which can be donated to charity. Posting credits and charitable donations should get others excited to do the same thing.

The at least one patient device 1610 is intended to represent one or more devices used by a potential patient to, among other things, provide content to social networks that, either due to explicit notification or scouring the social networks, are eventually included in the patient social network datastore 1608. Potential patients can be provided with assistance via the at least one patient device 1610. For example potential patients can gain access to rules and controls through a browser of the at least one patient device 1610, such as artificial agents that can select or facilitate selection of appropriate pictures and words or to reject inappropriate pictures and words.

The patient transaction engine 1612 is intended to represent hardware configured to convert a potential patient into a patient. The patient transaction engine 1612 utilizes any credits identifiable from the patient record datastore 1604 to assist a service provider in pricing and other factors when pitching services to the potential patient. In a specific implementation, the patient transaction engine 1612 corresponds to the patient transaction engine 312 of FIG. 3.

The scanning engine 1614 is intended to represent hardware configured to generate patient image data of a patient's body part (e.g., oral part, head part, etc.) using the image sensor 1615. In a specific implementation, the scanning engine 1614 corresponds to the patient scanning engine 204 and/or the practitioner 3D scanning engine 306 of FIGS. 2 and 3, respectively and the image sensor 1615 corresponds to the image sensor 206, the image sensor 307, and/or the image scanner 1504 of FIGS. 2, 3, and 15, respectively.

The segmentation engine 1616 is intended to represent hardware configured to perform segmentation of a patient's body state based on patient 3D image data of the patient. The segmentation engine 1616 may run in the background while a patient is involved in some other procedure or patient transaction. In a specific implementation, the segmentation engine 1616 corresponds to the segmentation engine 308 and/or the segmentation engine 1508 of FIGS. 3 and 15, respectively.

The initial and final position datastore 1618 is intended to represent a datastore to store initial and final position data for use by the patient transaction engine 1612 and medical device stage data for use by the starter device 3D printing engine 1620. The patient transaction engine 1612 acts as a treatment planning "hub" in communication with the patient compliance engine 1606, the image sensor 1615, and the 3D printer 1622. Advantageously, this enables communication between customers (patients) and a print-on-demand in the medical and beauty fields, such as dental and orthodontics. In a specific implementation, the initial and final position datastore 1618 corresponds to the final position datastore 310 and/or the original and final position datastore 1510 of FIGS. 3 and 15, respectively.

The starter device 3D printing engine 1620 is intended to represent hardware that receives communications from treatment planning engine, scanners, and the 3D printer 1622.

In an example of operation, a potential patient uses the at least one patient device 1610 to visit a website, download an app, or the like. The potential patient may order a kit for at-home preparation and scanning. Alternatively, the potential patient may go to a location that performs scanning services, such as a kiosk or a dental office. Once scanned, an stl file is created and sent to a treatment planning engine, a treatment plan is created, and the treatment plan is sent to doctor manufacturer who approves the treatment plan. The stl file is sent to a 3D printer, molds are printed, and devices, such as aligners, thermoformed. In the alternative, the stl file is sent to a 3D printer to print devices, such as aligners. Customers are API-pinged, social media sharing starts, and social media ambassadors are born. At point of consumer payment online or at the point of hitting print on 3D printer, customers are prompted to send a comment to stimulate social media regarding the services received. When 3D printing is done, a barcode/label is placed on the 3D printed device for UPS (or some other delivery service) and gets a tracking number, if the 3D printed devices are to be delivered.

Advantageously, when a doctor clicks print on his or her computer (send to printer) the back end is seamlessly controlled by the patient transaction engine and the patient compliance engine is handled for the doctor without input or assistance from the doctor. For example, when the mold begins to print, customers can be pinged with an electronic signal (serial number) that states that the customers aligners just started getting printed. Because patients have opted in for compliance the patient compliance engine can obtain a relevant picture, go to applicable social media sites, and post "Emily got a Smylio Smile" or the like, or the patient can be requested to post the same.

Figure 17:
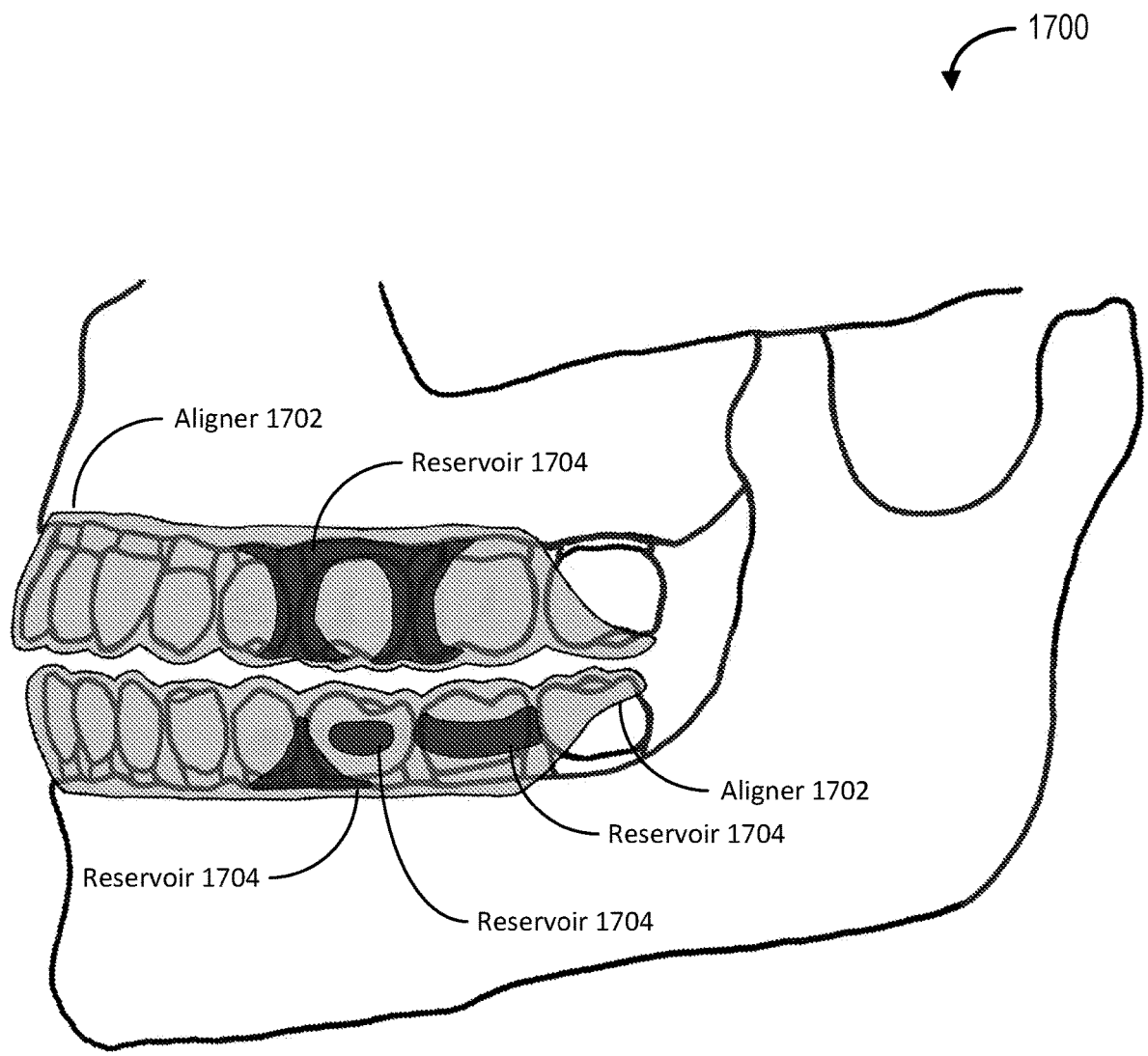
FIG. 17 is a conceptual diagram of a side view of a 4D full aligner.

FIG. 17 is a conceptual diagram 1700 of a side view of a 4D full aligner. The conceptual diagram 1700 includes a conceptual diagram of a skull with teeth (no reference numerals), an aligner 1702, and reservoirs 1704. In the example of FIG. 17, the aligner 1702 comprises a top aligner and a bottom aligner (collectively, "the aligner 1702"). The aligner 1702 is intended to represent an aligner that is operationally connected to substantially all of the teeth of a patient and can therefore be referred to as a "full aligner." The aligner 1702 can be referred to as a 4D aligner because it is a physical (3D) object with an additional ($4^{th}$) vector associated with the reservoirs 1704 through which medicine can be released over time. Advantageously, a reservoir or functionally similar structure can be built into a 3D printed medical device as part of a design process for a customized appliance. For an aligner, one or more reservoirs can be placed along the gum line, along the edges of teeth, between teeth, or along the surface of teeth, as is illustrated in the example of FIG. 17. It is noted that an aligner described here is not limited to a 4D aligner. For example, an aligner may be a 3D aligner having one or more reservoirs for chemicals that have medical effects (e.g., for halitosis, gingivitis, stimulate weight loss, etc.), either by being released therefrom or staying therein, or for a device, such as a sensor, that stays in the reservoir and monitors the patient's body state.

Figure 18:
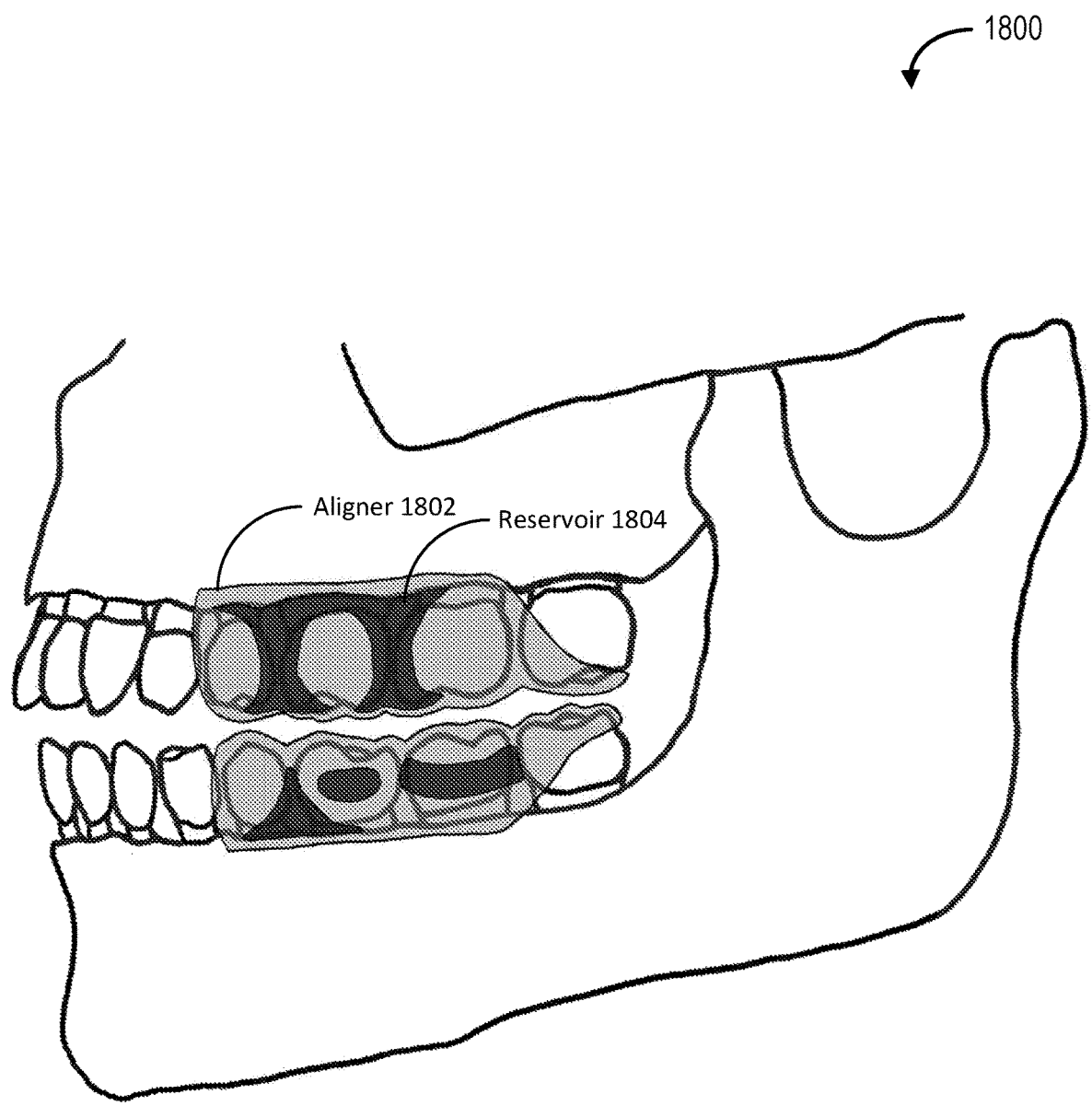
FIG. 18 is a conceptual diagram of a side view of a 4D partial aligner.

FIG. 18 is a conceptual diagram 1800 of a side view of a 4D partial aligner. The conceptual diagram 1800 includes a conceptual diagram of a skull with teeth (no reference numerals), an aligner 1802, and reservoirs 1804.

Figure 19:
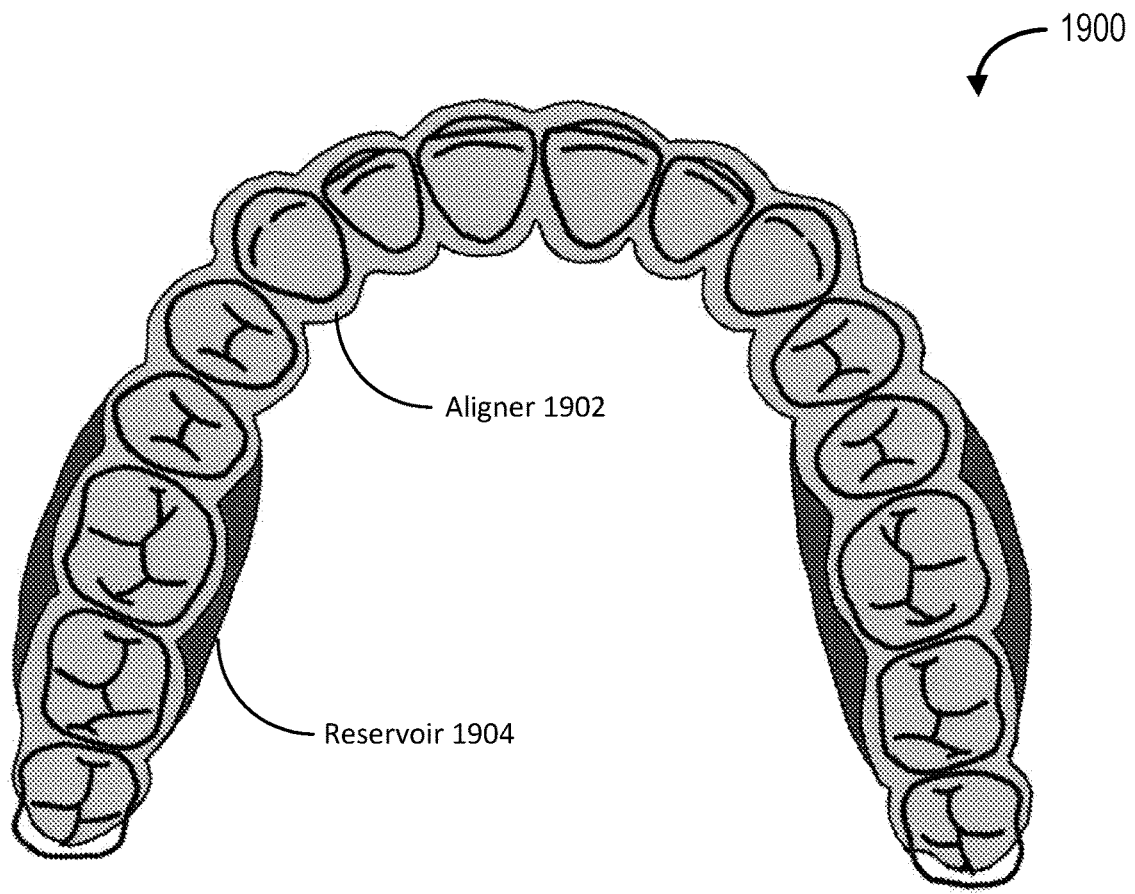
FIG. 19 is a conceptual diagram of top and bottom views of a 4D full aligner.
Figure 19:
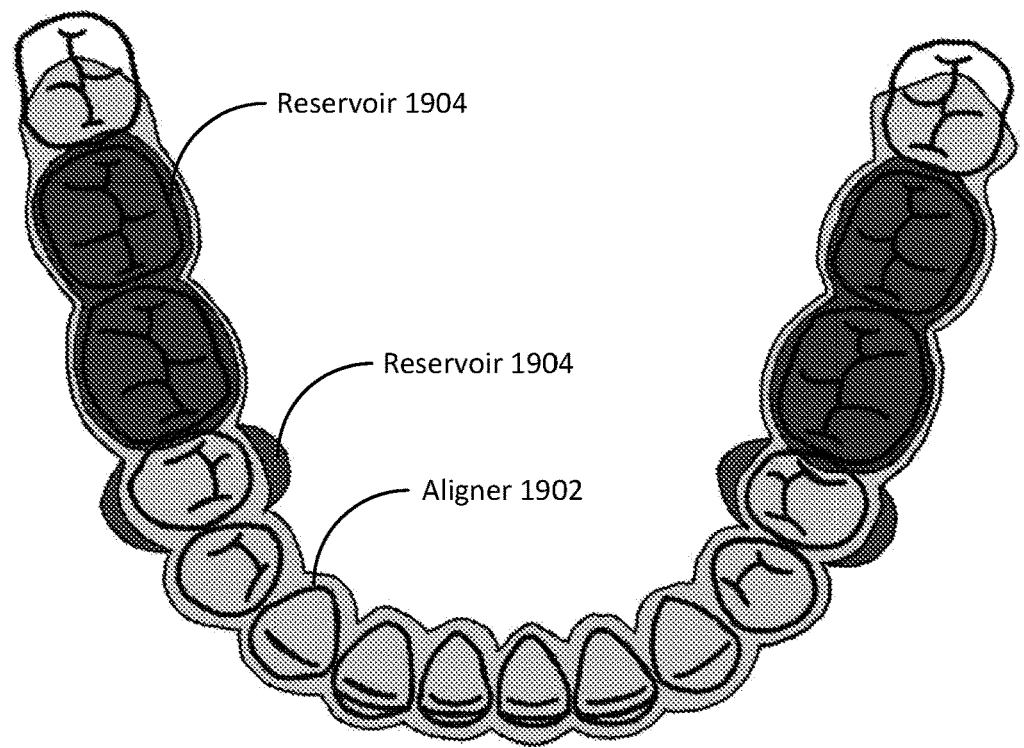

FIG. 19 is a conceptual diagram 1900 of top and bottom views of a 4D full aligner. The conceptual diagram 1900 includes a conceptual diagram of a skull with teeth (no reference numerals), an aligner 1902, and reservoirs 1904.

Figure 20:
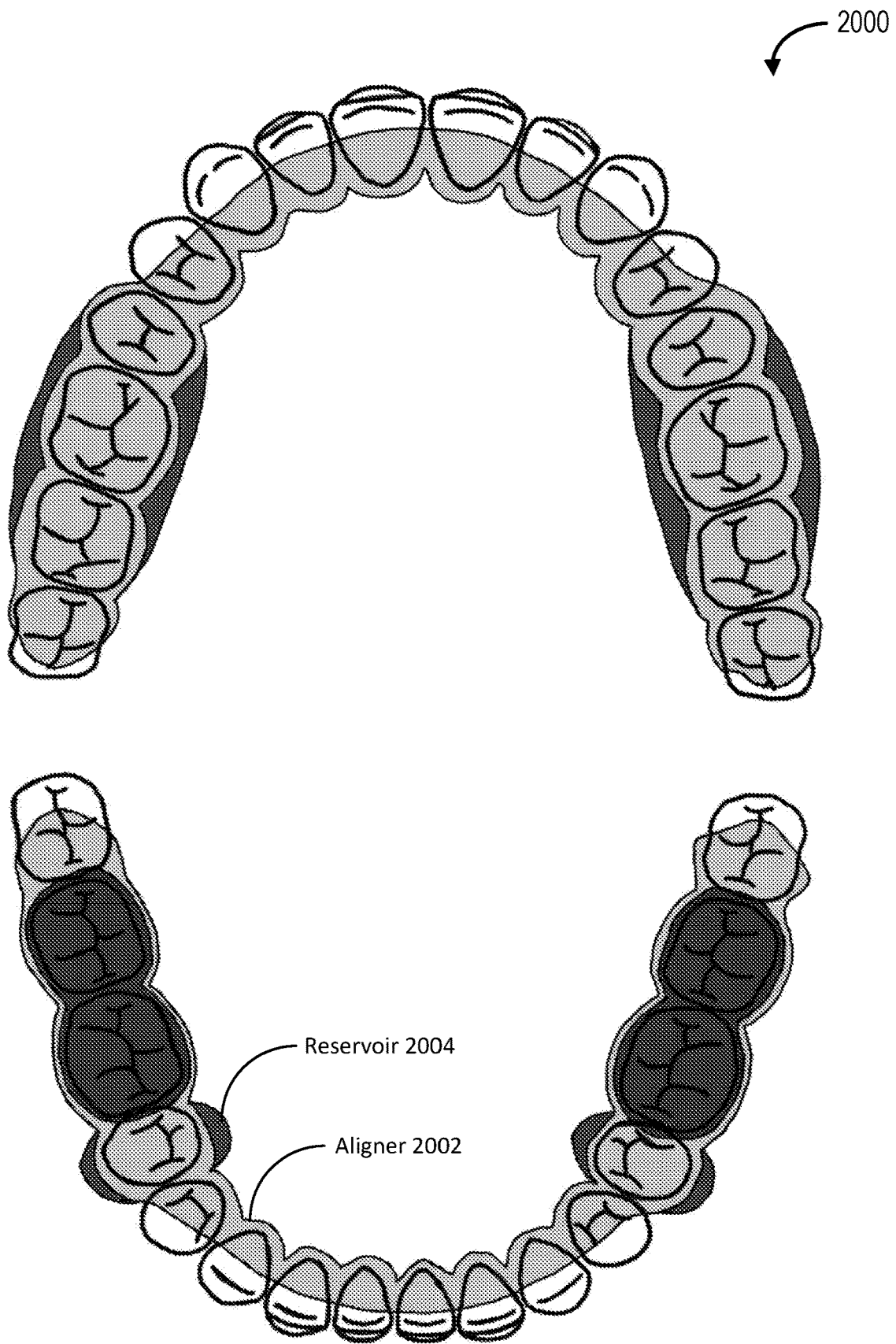
FIG. 20 is a conceptual diagram of top and bottom views of a 4D partial aligner.

FIG. 20 is a conceptual diagram 2000 of top and bottom views of a 4D partial aligner. The conceptual diagram 2000 includes a conceptual diagram of a skull with teeth (no reference numerals), an aligner 2002, and reservoirs 2004.

Figure 21:
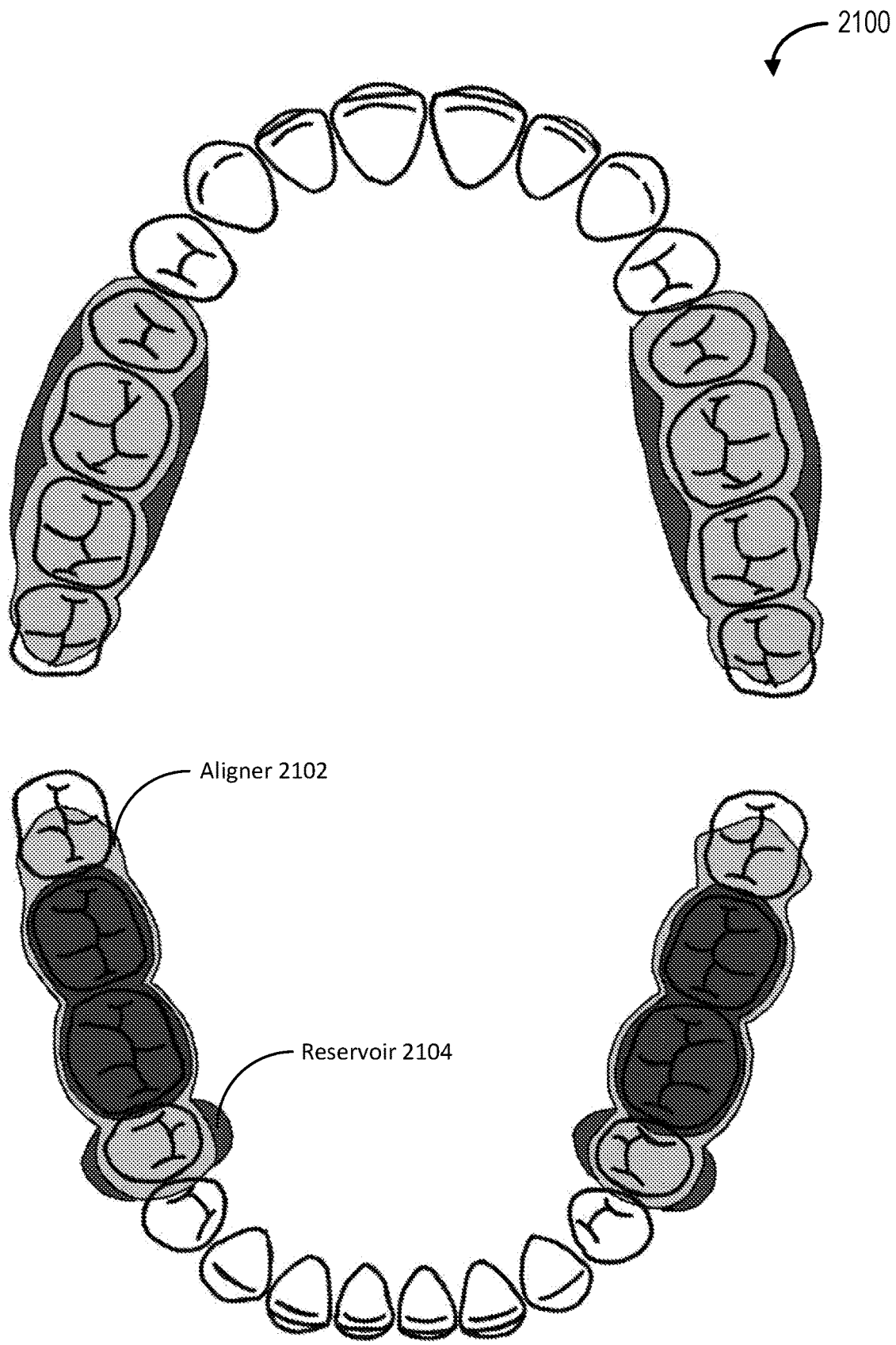
FIG. 21 is a conceptual diagram of top and bottom views of a 4D minimal aligner.

FIG. 21 is a conceptual diagram 2100 of top and bottom views of a 4D minimal aligner. The conceptual diagram 2100 includes a conceptual diagram of a skull with teeth (no reference numerals), an aligner 2102, and reservoirs 2104.

The entire workflow between the computer (treatment planning engine) and thermaformer and printer (including the material for the printer), as well as the direct fab process (direct fabrication of devices, such as aligners) can be managed using techniques described in this paper. These and other examples provided in this paper are intended to illustrate but not necessarily to limit the described implementation. As used herein, the term "implementation" means an implementation that serves to illustrate by way of example but not limitation. The techniques described in the preceding text and figures can be mixed and matched as circumstances demand to produce alternative implementations.

The invention claimed is:

1. A method for generating a three-dimensional (3D)-printed medical appliance treatment plan and providing a set of 3D-printed medical appliances based on the 3D-printed medical appliance treatment plan, the method comprising:

printing, using a 3D printing device based on a patient-specific shape formed to fit a body part of the patient, a starter 3D-printed medical appliance configured to cause initial movement of the body part of the patient, the starter 3D-printed medical appliance including a trial aligner medical appliance, the trial aligner comprising a no-movement tray, wherein the starter 3D-printed medical appliance is printed by the 3D printing device before the patient begins a 3D-printed medical appliance treatment plan;
generating a dynamic 3D-printed medical appliance treatment plan generation model;
obtaining a patient record for a patient;
receiving 3D scanning data of the patient;
generating the 3D-printed medical appliance treatment plan by applying the patient record and the 3D scanning data of the patient to the dynamic 3D-printed medical appliance treatment plan generation model, wherein the generating is based at least partially on the starter 3D-printed medical appliance;
providing the 3D-printed medical appliance treatment plan to a medical practitioner;
providing a manufacturing request to a manufacturer system for manufacturing a set of 3D-printed medical appliances;
manufacturing, in response to receiving the manufacturing request, the set of 3D-printed medical appliances;
providing the set of 3D-printed medical appliances to the patient;
receiving feedback from the medical practitioner regarding the 3D-printed medical appliance treatment plan;
modifying the dynamic 3D-printed medical appliance treatment plan generation model based on the feedback from the medical practitioner.

2. The method of claim 1, wherein the dynamic 3D-printed medical appliance treatment plan generation model includes an attribute selected from a group consisting of a pre-treatment state of the patient, an expected post-treatment state of the patient, a treatment timetable, expected pain levels, a budget range, and a combination of these.

3. The method of claim 1, wherein the 3D-printed appliance treatment plan includes an attribute selected from a group consisting of an expected post-treatment state of the patient, a treatment timetable, expected pain levels, an estimated cost, a type of 3D-printed medical appliances to be used for each of different phases of the 3D-printed medical appliance treatment plan, a design of 3D-printed medical appliances to be used for each of different phases of the 3D-printed medical appliance treatment plan, a manner of attaching the 3D-printed medical appliances, a duration of attaching the 3D-printed medical appliances, and a combination of these.

4. The method of claim 1, wherein the patient record includes 2D images of one or more body parts of the patient obtained by the patient using a mobile device.

5. The method of claim 1, wherein the 3D scanning data is obtained by scanning one or more body parts of the patient or scanning an impression of one or more body parts of the patient using a 3D scanning device.

6. The method of claim 1, wherein the modifying the dynamic 3D-printed medical appliance treatment plan generation model based on the feedback from the medical practitioner is performed using machine learning techniques.

7. The method of claim 1, wherein the 3D-printed medical appliances are 3D-printed dental appliances.

8. The method of claim 1, wherein the 3D-printed appliance treatment plan is provided to the medical practitioner for approval.

9. The method of claim 1, wherein the feedback from the medical practitioner includes manufacturer quality of service information.

10. A system for generating a 3D-printed medical appliance treatment plan and providing a set of 3D-printed medical appliances based on the 3D-printed medical appliance treatment plan, the system comprising:
a dynamic treatment plan generation model managing engine;
a patient record processing engine;
a treatment plan communicating engine;
a 3D printing device:
wherein, in operation:
the 3D printing device prints, based on a patient-specific shape formed to fit a body part of the patient, a starter 3D-printed medical appliance configured to cause initial movement of the body part of the patient, the starter 3D-printed medical appliance including a trial aligner medical appliance, the trial aligner comprising a no-movement tray, wherein the starter 3D-printed medical appliance is printed by the 3D printing device before the patient begins a 3D-printed medical appliance treatment plan:
the dynamic treatment plan generation model managing engine generates a dynamic 3D-printed medical appliance treatment plan generation model;
the patient record processing engine obtains a patient record for a patient;
the treatment plan communicating engine receives 3D scanning data of the patient;
the dynamic treatment plan generation model managing engine generates the 3D-printed medical appliance treatment plan by applying the patient record and the 3D scanning data of the patient to the dynamic 3D-printed medical appliance treatment plan generation model, wherein the generation is based at least partially on the starter 3D-printed medical appliance;
the treatment plan communicating engine provides the 3D-printed medical appliance treatment plan to a medical practitioner;
the treatment plan communicating engine provides a manufacturing request to a manufacturer system for manufacturing a set of 3D-printed medical appliances to be provided to the patient;
manufacturing, in response to receiving the manufacturing request, the set of 3D-printed medical appliances;
the treatment plan communicating engine receives feedback from the medical practitioner regarding the 3D-printed medical appliance treatment plan;
the dynamic treatment plan generation model managing engine modifies the dynamic 3D-printed medical appliance treatment plan generation model based on the feedback from the medical practitioner.

11. The system of claim 10, wherein the dynamic 3D-printed medical appliance treatment plan generation model includes an attribute selected from a group consisting of a pre-treatment state of the patient, an expected post-treatment state of the patient, a treatment timetable, expected pain levels, a budget range, and a combination of these.

12. The system of claim 10, wherein the 3D-printed appliance treatment plan includes an attribute selected from a group consisting of an expected post-treatment state of the patient, a treatment timetable, expected pain levels, an estimated cost, a type of 3D-printed medical appliances to be used for each of different phases of the 3D-printed medical appliance treatment plan, a design of 3D-printed medical appliances to be used for each of different phases of the 3D-printed medical appliance treatment plan, a manner of attaching the 3D-printed medical appliances, a duration of attaching the 3D-printed medical appliances, and a combination of these.

13. The system of claim 10, wherein the patient record includes 2D images of one or more body parts of the patient obtained by the patient using a mobile device.

14. The system of claim 10, further comprising a scanning engine, wherein in operation the scanning engine obtains the 3D scanning data by scanning one or more body parts of the patient or scanning an impression of one or more body parts of the patient using a 3D scanning device.

15. The system of claim 10, wherein in operation the dynamic treatment plan generation model managing engine modifies the dynamic 3D-printed medical appliance treatment plan generation model based on the feedback from the medical practitioner using machine learning techniques.

16. The system of claim 10, wherein the 3D-printed medical appliances are 3D-printed dental appliances.

17. The system of claim 10, further comprising a review and approval engine, wherein in operation the review and approval engine provides the 3D-printed appliance treatment plan to the medical practitioner for approval.

18. The system of claim 10, wherein the feedback from the medical practitioner includes manufacturer quality of service information.

19. A system for generating a 3D-printed medical appliance treatment plan and providing a set of 3D-printed medical appliances based on the 3D-printed medical appliance treatment plan, the system comprising:
   means for printing, using a 3D printing device based on a patient-specific shape formed to fit a body part of the patient, a starter 3D-printed medical appliance configured to cause initial movement of the body part of the patient, the starter 3D-printed medical appliance including a trial aligner medical appliance, the trial aligner comprising a no-movement tray, wherein the starter 3D-printed medical appliance is printed by the 3D printing device before the patient begins a 3D-printed medical appliance treatment plan;
   means for generating a dynamic 3D-printed medical appliance treatment plan generation model;
   means for obtaining a patient record for a patient;
   means for receiving 3D scanning data of the patient;
   means for generating the 3D-printed medical appliance treatment plan by applying the patient record and the 3D scanning data of the patient to the dynamic 3D-printed medical appliance treatment plan generation model, wherein the generating is based at least partially on the starter 3D-printed medical appliance;
   means for providing the 3D-printed medical appliance treatment plan to a medical practitioner;
   means for providing a manufacturing request to a manufacturer system for manufacturing a set of 3D-printed medical appliances to be provided to the patient;
   means for manufacturing, in response to receiving the manufacturing request, the set of 3D-printed medical appliances;
   means for receiving feedback from the medical practitioner regarding the 3D-printed medical appliance treatment plan;
   means for modifying the dynamic 3D-printed medical appliance treatment plan generation model based on the feedback from the medical practitioner.

* * * * *